(12) United States Patent
Alsberg et al.

(10) Patent No.: US 10,030,228 B2
(45) Date of Patent: *Jul. 24, 2018

(54) SCAFFOLD-FREE TISSUE CONSTRUCTS

(71) Applicant: Case Western Reserve University, Cleveland, OH (US)

(72) Inventors: Eben Alsberg, Cleveland, OH (US); Loran Solorio, Cleveland, OH (US); Phuong Dang, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/863,364

(22) Filed: Apr. 15, 2013

(65) Prior Publication Data

US 2014/0186952 A1 Jul. 3, 2014

Related U.S. Application Data

(60) Provisional application No. 61/623,654, filed on Apr. 13, 2012.

(51) Int. Cl.
*C12N 5/077* (2010.01)

(52) U.S. Cl.
CPC ........ *C12N 5/0655* (2013.01); *C12N 2501/15* (2013.01); *C12N 2506/1353* (2013.01); *C12N 2506/1384* (2013.01); *C12N 2533/54* (2013.01)

(58) Field of Classification Search
None
See application file for complete search history.

(56) References Cited

U.S. PATENT DOCUMENTS

| 2011/0151565 A1* | 6/2011 | Hase et al. .................. 435/401 |
| 2011/0208276 A1 | 8/2011 | Machold et al. |
| 2012/0141547 A1 | 6/2012 | Zhao et al. |
| 2012/0329157 A1* | 12/2012 | Nakamura .................. 435/397 |

FOREIGN PATENT DOCUMENTS

| WO | WO 2008143149 A1 * | 11/2008 |
| WO | WO 2011108517 A1 * | 9/2011 |

OTHER PUBLICATIONS

Ogawa et al., In vitro proliferation and chondrogenic differentiation of rat bone marrow stem cells cultured with gelatin hydrogel microspheres for TGF-β1 release, 2010, Journal of Biomaterials Science, Polymer Edition 21(5): 609-621.*
Han et al., Cartilage regeneration using adipose-derived stem cells and the controlled-released hybrid microspheres, 2010, Joint Bone Spine 77(1): 27-31.*
Solorio et al., Gelatin microspheres crosslinked with genipin for local delivery of growth factors, 2010, Journal of tissue engineering and regenerative medicine 4(7): 514-523.*
Murdoch, Alan D., et al. "Chondrogenic Differentiation of Human Bone Marrow Stem Cells in Transwell Cultures: Generation of Scaffold-Free Cartilage." Stem cells 25.11 (2007): 2786-2796.*

* cited by examiner

*Primary Examiner* — Robert J Yamasaki
(74) *Attorney, Agent, or Firm* — Tarolli, Sundheim, Covell & Tummino LLP

(57) ABSTRACT

A tissue construct comprising includes a self-assembled, scaffold-free, high-density cell aggregate. The cell aggregate includes a plurality of cells and a plurality of biocompatible and degradable nanoparticles and/or microparticles that are incorporated within the cell aggregate. The nanoparticles and/or microparticles act as a bulking agent and/or provide bioactive agents or signals within the cell aggregate to increase the cell aggregate size and/or thickness and improve the mechanical properties of the cell aggregate and/or regulate cell function within the aggregate allowing the cell aggregate to be readily manipulated and formed into tissue constructs with defined architectures and potential tissue specific functionality.

5 Claims, 16 Drawing Sheets

Figs. 1A-B

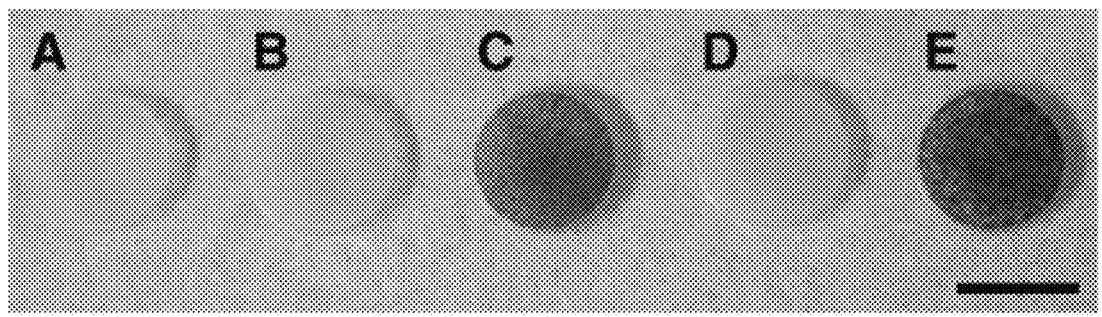
Figs. 4A-E

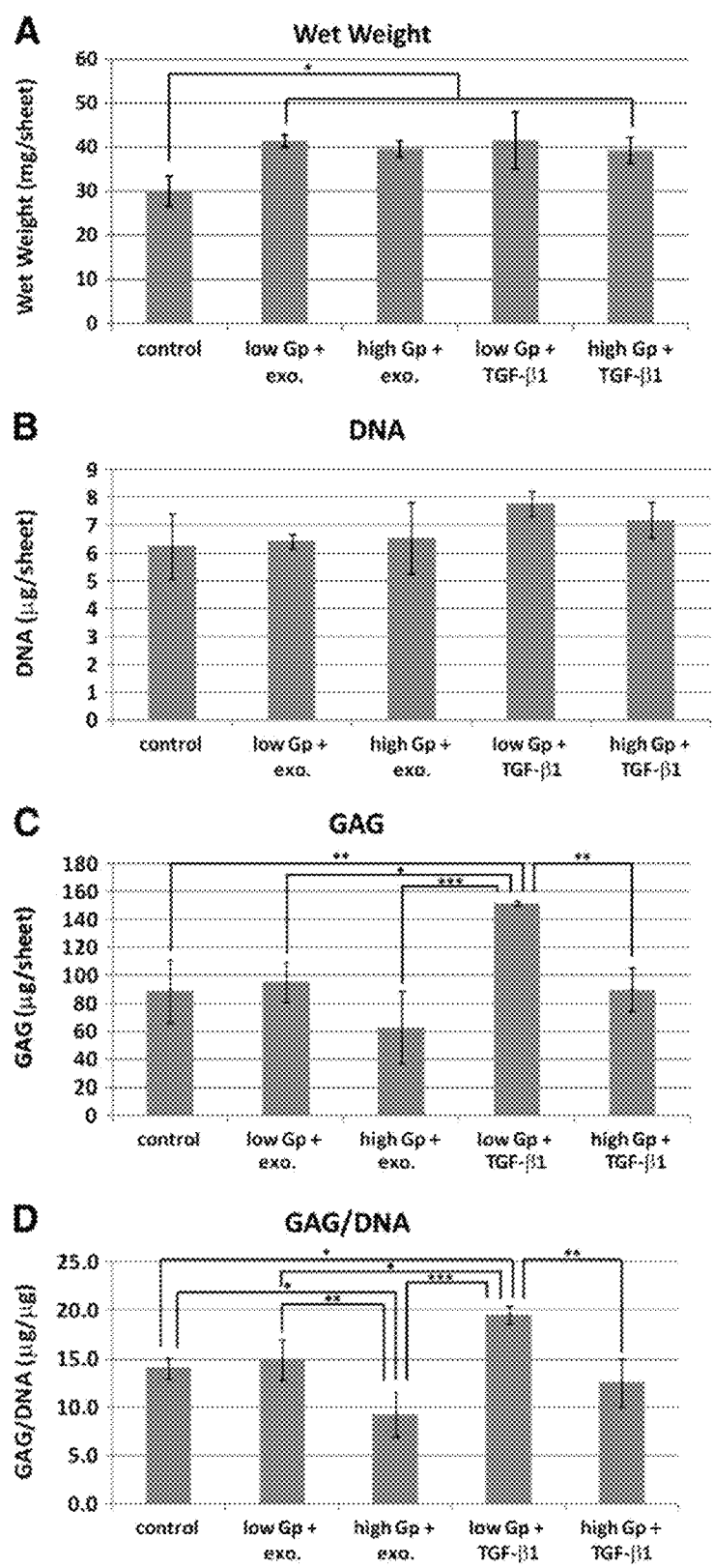
Figs. 5A-D

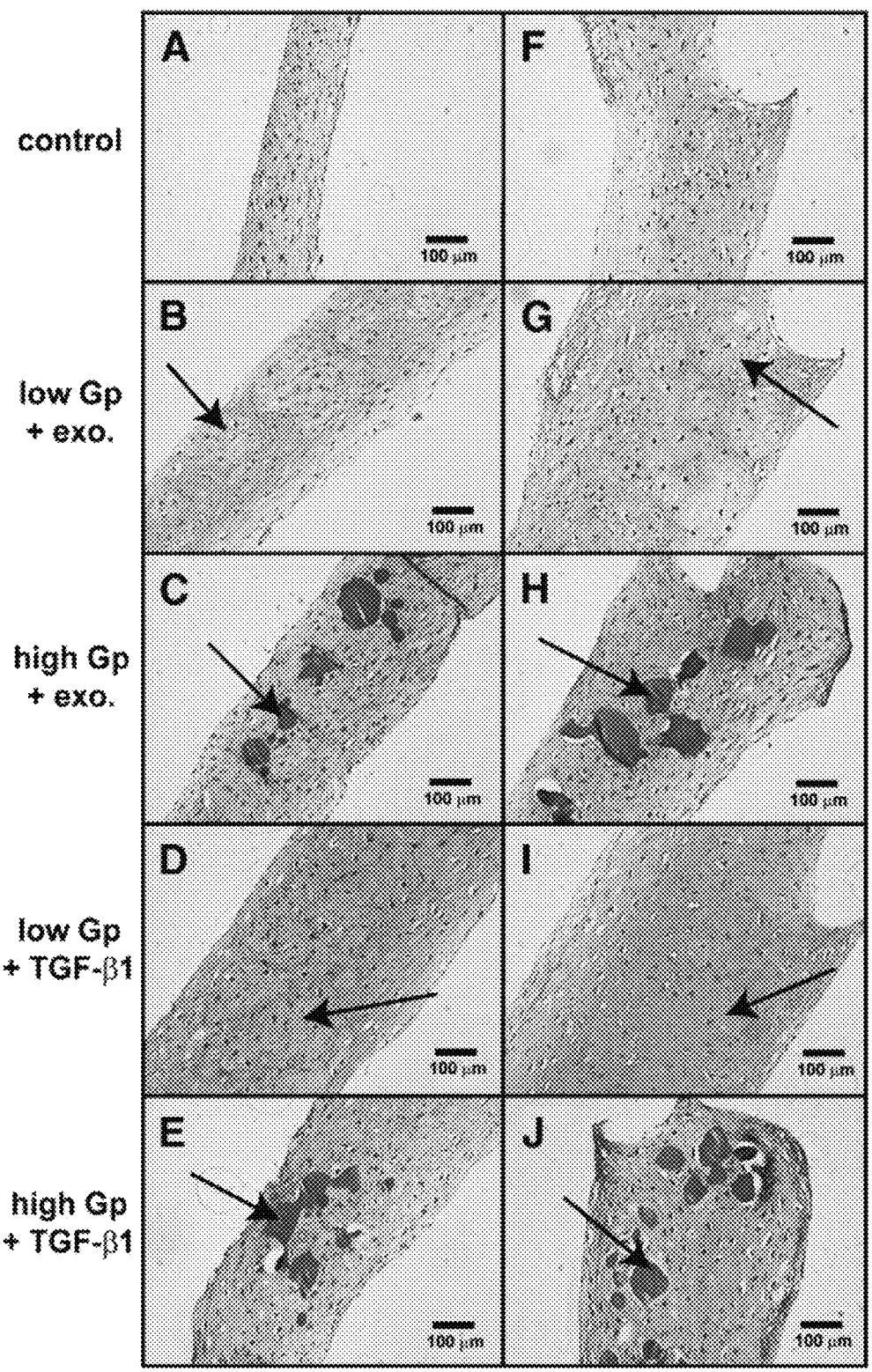
Figs. 6A-J

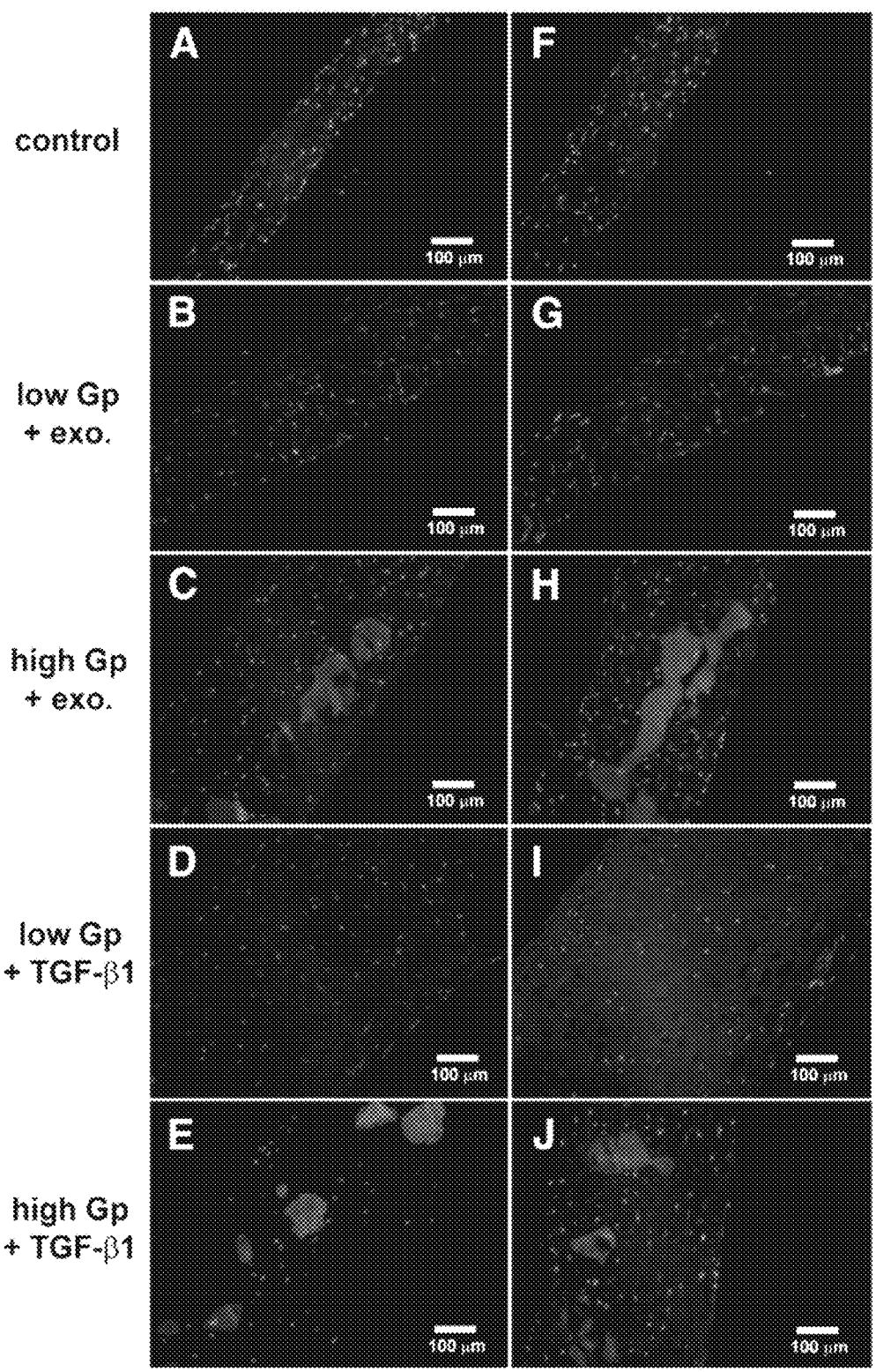
Figs. 7A-J

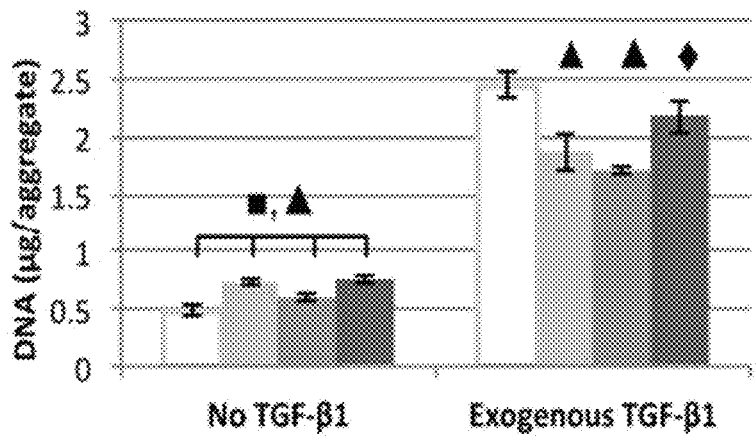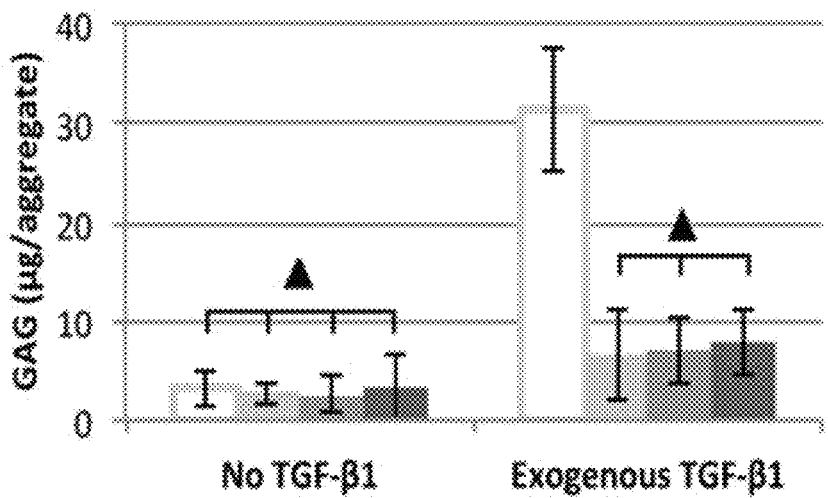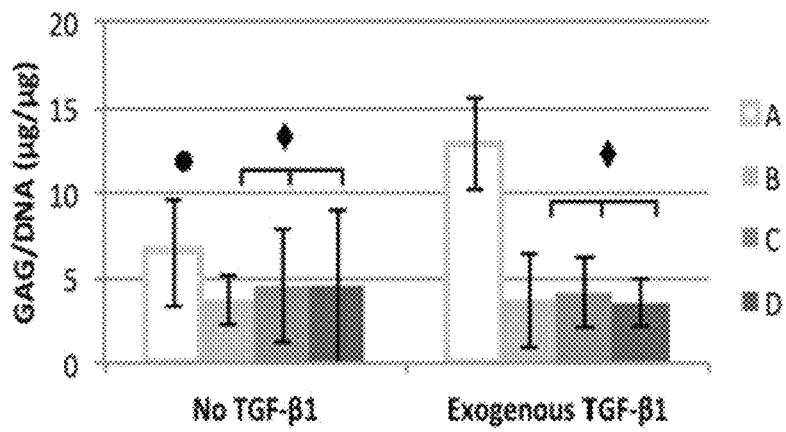
Figs. 8A-C

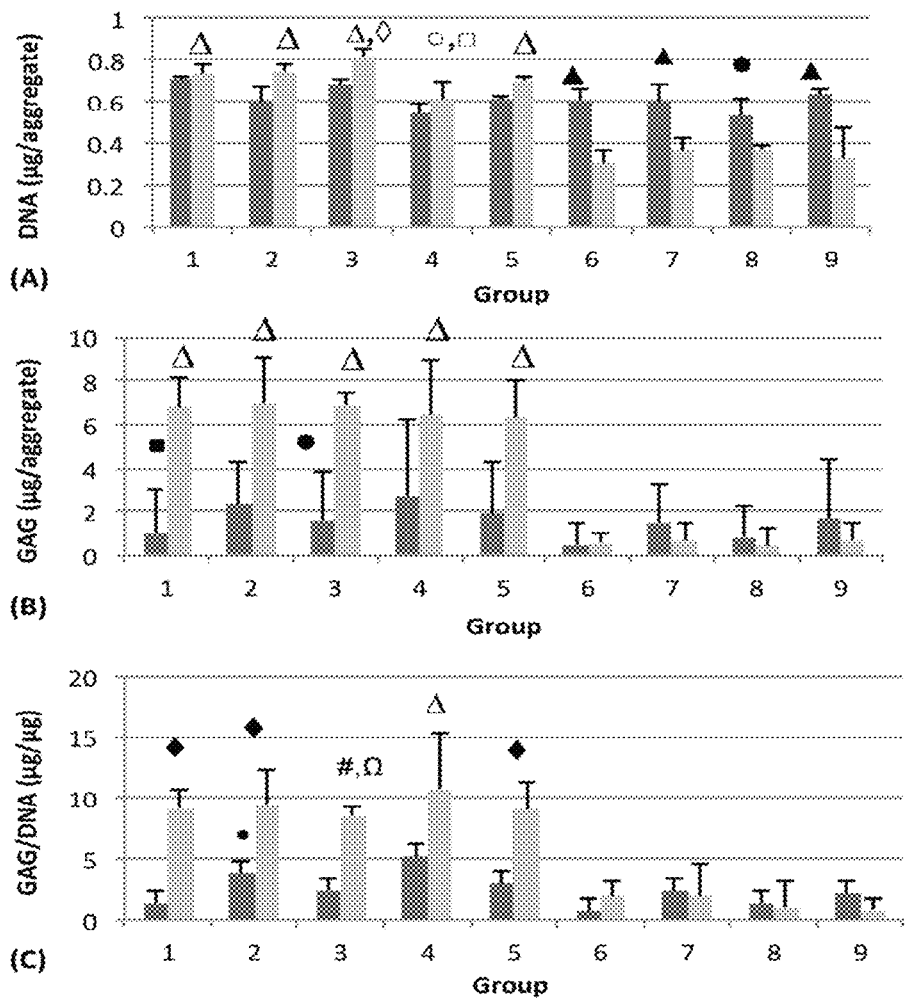
Figs. 9A-C

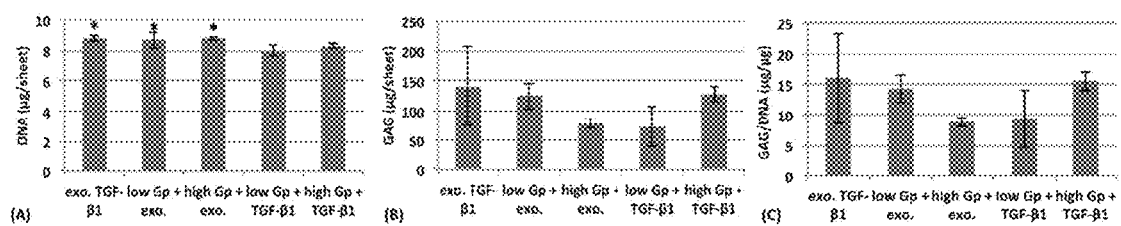
Figs. 10A-C
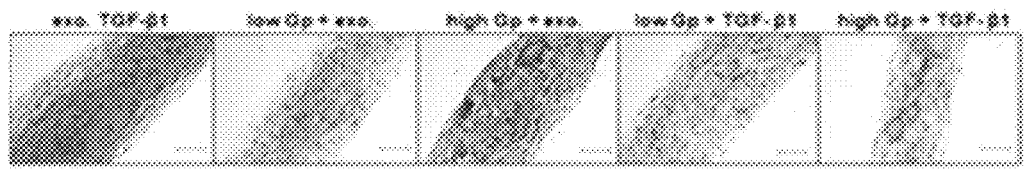
Fig. 11

SCAFFOLD-FREE TISSUE CONSTRUCTS

RELATED APPLICATION

This application claims priority from U.S. Provisional Application No. 61/623,654, filed Apr. 13, 2012, the subject matter, which is incorporated herein by reference in its entirety.

TECHNICAL FIELD

The present invention generally relates to tissue engineering, bioactive factor delivery, and disease therapeutics, and more particularly relates to scaffold-free tissue constructs and methods of forming the tissue constructs.

BACKGROUND

Osteoarthritis (OA) is a degenerative disease of the articular cartilage affecting millions of people worldwide. As no current treatment can fully and consistently restore normal joint function to patients afflicted with OA, there is a significant clinical need for alternative therapies for cartilage regeneration. Many approaches to the tissue engineering of articular cartilage involve the use of cells in combination with soluble bioactive factors and biomaterials that may provide specific microenvironmental cues for chondrogenic induction. Mesenchymal stem cells (MSCs) from bone marrow have been shown to be a promising cell source for these cartilage tissue engineering strategies, as they can be expanded in culture without losing multipotency, and can differentiate into many cell types of the connective tissue lineage including chondrocytes under appropriate conditions. Specifically, two important factors for the in vitro chondrogenic induction of MSCs are high initial cell density and exposure to transforming growth factor β (TGF-β).

Several in vitro culture methods have been developed for MSC chondrogenesis, including aggregate or pellet culture, micromass culture, and self-assembling cell sheet systems. These culture systems take advantage of the abundant cell-cell interactions that occur in 3D high density culture, without the potential interference of a biomaterial scaffold. In particular, self-assembling cell sheets show promise for use in cartilage tissue engineering applications, as they may form larger constructs with much greater surface areas and volumes than aggregates or tiny micromass cultures. Unlike spherical cell aggregates, which are limited in size by the diffusion distance of nutrients into the center of the sphere, flat sheets of various dimensions can be formed without necessitating a proportional increase in construct thickness, enabling nutrient diffusion to all regions of the tissue. Upon surgical evaluation, chondral defects in the knee have an area of at least 0.5 cm2, with over a third of the defects having areas of at least 1 $cm^2$. Self-assembling sheets could be clinically practical for the treatment of these defects, as sheets of the appropriate size could be formed and then implanted into a defect as an intact piece. This is in contrast to smaller cell constructs, which may not be as readily applied for the clinical treatment of cartilage defects since a number of constructs would be required to fill a single lesion. It may be difficult to localize multiple constructs to a defect, and in order to repair the damaged cartilage, the individual cell constructs would have to integrate with each other as well as with the surrounding host tissue.

SUMMARY

Embodiments described herein relate tissue constructs that can be used for the promotion of tissue repair and bio-artificial tissue engineering. The tissue constructs can be formed or derived from self-assembled, scaffold-free, high density cell aggregates. The self-assembled, scaffold-free high density cell aggregate can include a population or plurality of cells and plurality of nanoparticles and/or microparticles that are incorporated within the cell aggregate. The nanoparticles and/or microparticles can act as a bulking agent within the cell aggregate to increase the cell aggregate size and/or thickness. Incorporation of the nanoparticles and/or microparticles in the cell aggregate can also improve the mechanical properties of the cell aggregate formed from the cells and nanoparticles and/or microparticles allowing the cell aggregate to be readily manipulated and formed into tissue constructs with defined architectures, such as sheets, oblate spheroids, spheroids, or potentially any other shape. The nanoparticles and/or microparticles can potentially enhance cell function, such as differentiation, and/or enhance or accelerate tissue formation In some embodiment, the nanoparticles and/or microparticles that are dispersed in cell aggregate can be formed from a biocompatible and biodegradable material that is capable of improving properties of the cell aggregate and which upon degradation is substantially non-toxic.

In other embodiments, the nanoparticles and/or microparticles can have a diameter less than 1 mm and typically between about 1 nm and about 200 μm, e.g., about 20 μm to about 100 um. The nanoparticles and/or microparticles can include both microspheres and microcapsules, and may have an approximately spherical or polygonal geometry and be of fairly uniform size. The size and shape of the nanoparticles and/or microparticles dispersed in the cell aggregate can vary to adjust the mechanical properties of the cell aggregate and tissue construct formed from the cell aggregate.

In some embodiments, the nanoparticles and/or microparticles dispersed in the cell aggregate can have substantially uniform diameters; while in other embodiments, the diameters of the nanoparticles and/or microparticles dispersed can vary.

In other embodiments, the nanoparticles and/or microparticles can be formed from a biocompatible and biodegradable polymer. In one example, the biodegradable polymer can include a hydrogel that comprises natural macromers, which can be cross-linked to vary the mechanical properties and/or degradation profile of the nanoparticles and/or microparticles.

In some embodiments, the nanoparticles and/or microparticles can include at least one bioactive agent that is differentially and/or controllably released by the nanoparticles and/or microparticles.

In some embodiments, the bioactive agent can be physically associated with the nanoparticles and/or microparticles and spatially and/or temporally released with a defined release profile from the nanoparticles and/or microparticles. In some embodiments, the bioactive agent can induce the formation of a cell sheet, graft, or structure. One example of the bioactive that can be used to induce the formation of a cell sheet, graft, or structure belongs to the Transforming Growth Factor family (TGF) (e.g., TGF-β1).

In other embodiments, the cell aggregate is a self-assembled cell sheet that comprises undifferentiated and/or substantially differentiated progenitor cells, a plurality of nanoparticles and/or microparticles, and a self-secreted extracellular matrix of the undifferentiated and/or substantially differentiated progenitor cells that can bind to or permit the adhesion of cells in the aggregate. The self-secreted extracellular matrix of the cells that can include compounds selected from the group consisting of proteins like collagen; proteoglycan; glycoprotein; gycosaminoglycan, or any combination thereof.

In another embodiment, the cell aggregate includes at least about 50%, at least about 60%, at least about 70%, at least about 80% cells based on the total volume of the cell aggregate.

In still another embodiment, the tissue construct can be free of cells, i.e., an acellular product of the cell aggregate. The composition or the structure of the cell aggregate free of cell or the acellular sheet is the same as the cell aggregate as disclosed herein but is free of cell. The acellular tissue construct can be used alone or in combination with other cell types or growth factors for the promotion of tissue repair or tissue engineering application.

In another embodiment, the progenitor cell is an adult stem cell. The stem cell, such as an adult stem cell, can be isolated from animal or human tissues. The stem cell used for the production of the cell sheet can be autologous, allogeneic, or xenogeneic. In the embodiments, the stem cell is isolated from, but not limited to, tendon/ligament tissue, bone morrow, adipose tissue or dental pulp.

In other embodiments, the cell aggregate is formed by a method comprising the steps of isolating undifferentiated and/or substantially differentiated progenitor cells, expanding the undifferentiated and/or substantially differentiated progenitor cells, combining the undifferentiated and/or substantially differentiated progenitor cells with a plurality of the nanoparticles and/or microparticles so that the nanoparticles and/or microparticles are dispersed with the undifferentiated and/or substantially differentiated progenitor cells, and culturing the dispersion of nanoparticles and/or microparticles and undifferentiated and/or substantially differentiated progenitor cells so that an cell aggregate is formed, by cell-cell interactions and cell-nanoparticle and/or microparticle interactions. The cell aggregate can include an extracelluar matrix that can bind to or permit the adhesion of cells in the aggregate.

In still another embodiment, by genetic modification, the undifferentiated and/or substantially differentiated progenitor cells is able to over-express bioactive agents. In another embodiment for formation of cartilage, the cell aggregate can be adhered to another cell aggregate, layered, mechically manipulated, for example by compressive forces, or further modified to accelerate or improve formation of the cartilage. In still another alternative embodiment for bone healing, tensile load is applied to the cell aggregate to assist the healing of bone or tendon or ligament.

In still other embodiments, a heterogenous cell aggregate or tissue construct can be formed that includes defined regions or portion (e.g., layers) of differing or similar cell aggregate materials. The differing regions or portions of the heterogenous cell aggregate or tissue construct can be provided or formed with or without nanoparticles and/or microparticles and can have similar or different properties to vary the properties of the tissue construct for particular tissue engineering applications.

BRIEF DESCRIPTION OF THE DRAWINGS

FIG. 4 illustrates cartilage sheets harvested from membranes after 3 weeks. Left to right: A. control, B. low Gp+exo., C. high Gp+exo., D. low Gp+TGF-β1, and E. high Gp+TGF-β1. The dark blue color in the high Gp microsphere-containing sheets is due to remaining undegraded microspheres. (Scale bar=10 mm).

FIG. 5 Wet weights (A), DNA contents (B), GAG contents (C), and GAG per DNA (D) of harvested sheets. *pb0.05, pb0.01, *pb0.001.

FIG. 6 illustrates photomicrographs of Safranin-O/Fast Green stained cross-sections from the central (A-E) and edge (F-J) regions of sheets. Orange stain indicates the presence of GAG. Arrows indicate cell and matrix-filled regions where low Gp microspheres degraded (B, G and D, I) or the presence of residual high Gp microspheres (C, H and E, J). (For interpretation of the references to color in this figure legend, the reader is referred to the web version of this article).

FIG. 7 illustrates photomicrographs of immunofluorescence staining of cross-sections from the central regions of sheets. Green fluorescence indicates the presence of type I collagen (A-E) or type II collagen (F-J). Bright green residual high Gp microspheres can be observed in C, H and E, J due to autofluorescence of the crosslinked gelatin. (For interpretation of the references to color in this figure legend, the reader is referred to the web version of this article).

FIG. 8 illustrates hASC donor screen. (A) DNA, (B) GAG and (C) GAG/DNA contents at 3 weeks for 4 different donors. ■: Significantly lower (p<0.001) than "exogenous TGF-β1" group from the same donor. ▲: Significantly lower (p<0.001) than "exogenous TGF-β1" group from donor A. ◆: Significantly lower (p<0.01) than "exogenous TGF-β1" group from donor A. •: Significantly lower (p<0.05) than "exogenous TGF-β1" group from donor A. 140×29 mm (300×300 DPI).

FIG. 9 illustrates photomicrographs of low Gp (A) and high Gp (B) crosslinked gelatin microspheres hydrated in PBS, and (C) microsphere size histograms showing the frequency of microsphere size in 20 μm intervals. Scale bar=50 μm. 56×42 mm (300×300 DPI).

FIG. 10 illustrates hASC (donor A) aggregate study. (A) DNA, (B) GAG, and (C) GAG/DNA content of hASC aggregates at 1 (dark gray) and 2 (light gray) weeks. •: Significantly different (p<0.05) from week 2 time point of group. ■: Significantly different (p<0.01) from week 2 time point of group. ▲: Significantly different (p<0.001) from week 2 time point of group. ◇: Significantly higher (p<0.01) than group 4 at week 2. ○: Significantly higher (p<0.01) than group 8 at week 2. □: Significantly higher (p<0.001) than groups 6, 7, and 9 at week 2. Δ: Significantly higher (p<0.001) than groups 6 through 9 at week 2. •: Significantly higher (p<0.01) than groups 6 through 9 at week 2. #: Significantly higher (p<0.05) than groups 6 and 7 at week 2. 5: Significantly higher (p<0.01) than groups 8 and 9 at week 2. 90×90 mm (300×300 DPI).

FIG. 11 illustrates hASC (donor A) sheet study. (A) DNA, (B) GAG, and (C) GAG/DNA content of hASC sheet constructs after 3 weeks in culture. *: Significantly higher (p<0.05) than "low Gp+TGF-β1" group. 140×29 mm (300×300 DPI).

DETAILED DESCRIPTION

Figure 1:
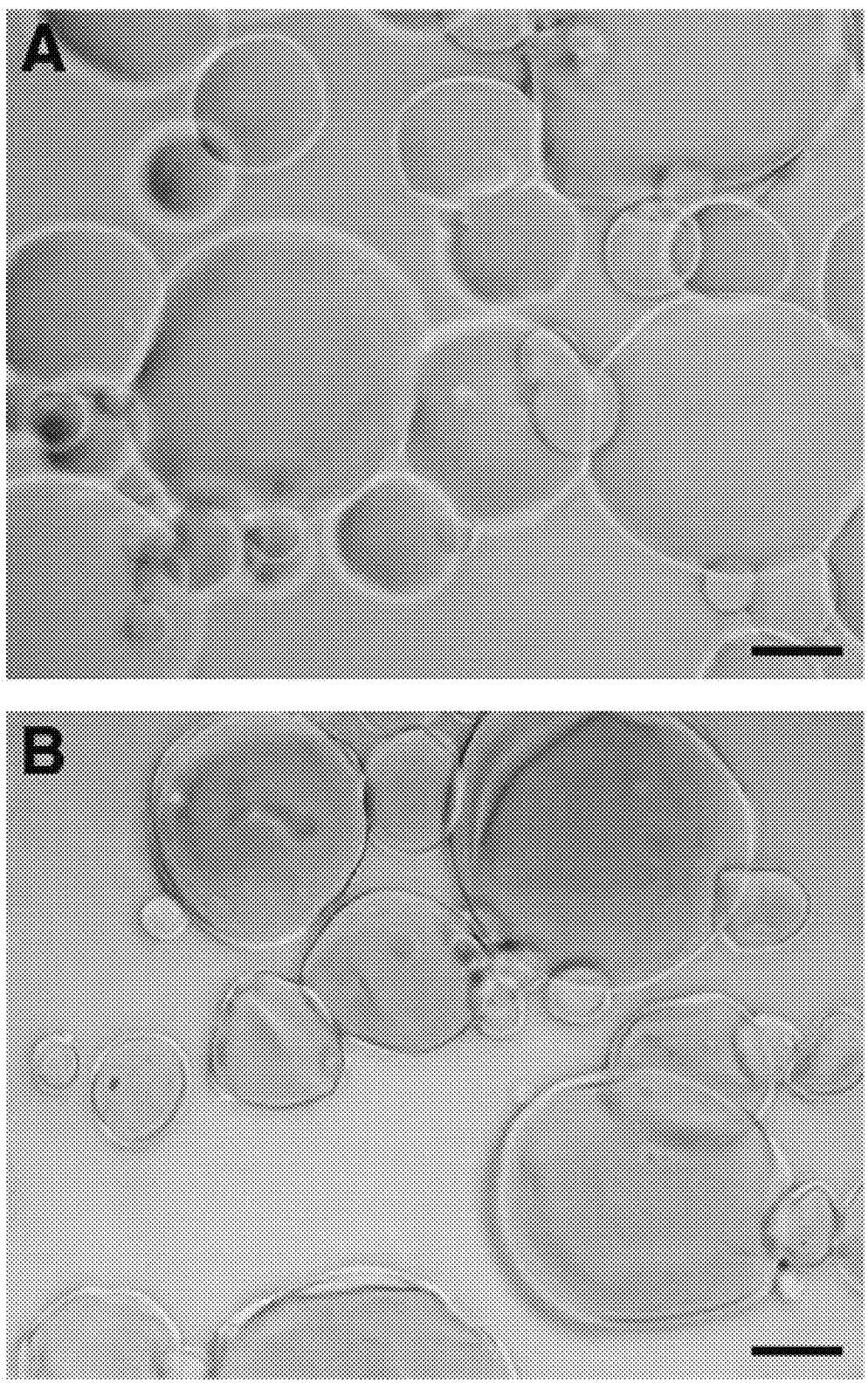
FIG. 1 illustrates light photomicrographs of low Gp (A) and high Gp (B) microspheres hydrated in PBS. (Scale bar=50 μm).

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "bioactive agent" can refer to any agent capable of promoting tissue formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "carrier material" can refer to a material capable of transporting, releasing, and/or complexing at least one bioactive agent.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, miRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "aggregate" can refer to a group or cluster comprising at least two or more cells (e.g., progenitor and/or differentiated cells).

As used herein, the term "population" can refer to a collection of cells, such as a collection of progenitor and/or differentiated cells.

As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage or in different lineages.

Embodiments described herein relate to tissue constructs that can be used for the promotion of tissue repair and bio-artificial tissue engineering. The tissue constructs are formed or derived from self-assembled, scaffold-free high density cell aggregates. By high density cell aggregates, it is meant the cell aggregate has a cell density of at least about $1\times10^5$ cells/ml in cell growth medium, for example, at least about $1\times10^6$ cells/ml, at least about $1\times10^7$ cells/ml, at least about $1\times10^8$ cells/ml, at least about $1\times10^9$ cell/ml, or at least about $1\times10^{10}$ cell/ml in cell growth medium.

By scaffold-free, it is meant the cells are not seeded in a natural or artificial continuous polymer matrix scaffold that defines the area or volume or at least a portion of the area or volume of the cell aggregate. A scaffold-free cell aggregated as used herein is meant to distinguish the cell aggregate from engineered tissue constructs in which the cells are seeded or embedded into a continuous polymer matrix or scaffold, such as a hydrogel, that encompasses the cells. In contrast, a scaffold-free cell aggregate can include discrete or regions of polymer or matrix materials that are intermixed with the cells and can be in the form of nanoparticles and/or microparticles.

By self-assembled, it is meant that the cells can aggregate or assemble spontaneously or by themselves and without mechanical manipulation while in culture into cell aggregates having defined shapes, such as sheets. Such assembly can be caused by cell-cell interactions, interactions with the particles, or formation of a self-secreted extracellular matrix that can bind to or permit the adhesion of cells in the aggregate.

The self-assembled, scaffold-free, high density cell aggregate can include a population of cells and a plurality of nanoparticles and/or microparticles that are dispersed with the cells within the cell aggregate. The cell aggregate can also include extracellular matrix material that is secreted by the cells and adheres or binds the cells and nanoparticles and/or microparticles. In some embodiments, the extracellular matrix can include collagen; proteoglycan; glycoprotein; glycosaminoglycan (GAG); as well as other extracellular matrix proteins.

The cells used to form the cell aggregate can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to mixing with the nanoparticles and/or microparticles. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

In some embodiments, the cell can be an undifferentiated or substantially differentiated progenitor cell. In other embodiments, the progenitor cell can be an adult stem cell. The stem cell, such as an adult stem cell, can be isolated from animal or human tissues. The stem cell used for the production of the cell sheet can be autologous or allogeneic. In the embodiments described herein, the stem cell can isolated from, but not limited to, tendon/ligament tissue, bone morrow, adipose tissue or dental pulp. The cell aggregate can include at least about 50%, at least about 60%, at least about 70%, at least about 80% cells based on the total volume of the cell aggregate.

The nanoparticles and/or microparticles dispersed with the cells can act as a bulking agent within the cell aggregate to increase the cell aggregate size (e.g., thickness). Incorporation of the nanoparticles and/or microparticles in the cell aggregate can also improve the mechanical properties (e.g., compressive equilibrium modulus and tensile strength) of the cell aggregate and enable more uniform extracellular matrix deposition compared to cell aggregates without the nanoparticles and/or microparticles. This allows the cell aggregate to be readily manipulated and formed into tissue constructs with defined architectures. The nanoparticles and/or microparticles can also potentially enhance cell function, such as differentiation, and/or enhance or accelerate tissue formation.

The nanoparticles and/or microparticles that are dispersed in the cell aggregate can be formed from a biocompatible and biodegradable material that is capable of improving properties of the cell aggregate and which upon degradation is substantially non-toxic. The microparticles can have a diameter less than 1 mm and typically between about 1 nm and about 200 µm, e.g., about 20 µm to about 100 µm. The nanoparticles and/or microparticles can include nanospheres, nanocapsules, microspheres, and microcapsules, and may have an approximately spherical geometry and be of fairly uniform size. The size and shape of the nanoparticles and/or microparticles dispersed in the cell aggregate can vary to adjust the mechanical properties of the cell aggregate and tissue construct formed from the cell aggregate. In some embodiments, the nanoparticles and/or microparticles dispersed in the cell aggregate can have substantially uniform diameters; while in other embodiments, the diameters of the dispersed nanoparticles and/or microparticles can vary.

The nanoparticles and/or microparticles can include nanospheres and/or microspheres that have a homogeneous composition as well as nanocapsules and/or microcapsules, which include a core composition (e.g., a bioactive agent) distinct from a surrounding shell. For the purposes of the present invention, for the purposes of the present invention, the terms "nanosphere," "nanoparticle," and "nanocapsule" may be used interchangeably, and the terms "microsphere," "microparticle," and "microcapsule" may be used interchangeably.

In some embodiments, the nanoparticles and/or microparticles can be formed from a biocompatible and biodegradable polymer. Examples of biocompatible, biodegradable polymers include natural polymers, such as collagen, fibrin, gelatin, glycosaminoglycans (GAG), poly(hyaluronic acid), poly(sodium alginate), alginate, hyaluronan, and agarose. Other examples of biocompatible, biodegradable polymers are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Still other examples of materials that may be used to form nanoparticles and/or microparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), polyhydroxybutyrate (PHB), copolymers thereof, and blends thereof.

In some embodiments, the biocompatible and biodegradable polymer is a biodegradable hydrogel, such as gelatin. The biodegradable hydrogel can include a plurality of natural macromers that can be cross-linked using a cross-linking agent to provide a plurality of cross-links. Various sugar derivatives, such as glyoxal, D-ribose, or genipin can be used to cross-link the hydrogel. Other cross-linking agents, such as glutaraldehyde, can also be used. Concentrations of the crosslinking agent as well as time and temperature used for crosslinking can be varied to obtain the optimal results The number or percentage of cross-links linking the macromers can be varied to control the mechanical properties, swelling ratios, and degradation profiles of the hydrogel and nanoparticles and/or microparticles. The percentage of cross-links can be varied between about 1% and about 70% by weight, and, for example, between about 20% and about 75% by weight. By increasing the percentage of cross-links, for example, the degradation rate of the biodegradable hydrogel can be decreased. Additionally, the compressive stiffness of the biodegradable hydrogel can be increased by increasing the percentage of cross-links. Further, the swelling behavior of the biodegradable hydrogel can be increased by decreasing the percentage of cross-links. It should also be appreciated that the macromer scaffold can be in either a hydrated or lyophilized state to enhance the addition of bioactive agents.

The nanoparticles and/or microparticles can also be modified to enhance cell function, such as differentiation, and/or enhance or accelerate tissue formation as promote cell adhesion. For example, the nanoparticles and/or microparticles can include at least one attachment molecule to facilitate attachment of at least one cell thereto. The attachment molecule can include a polypeptide or small molecule, for example, and may be chemically immobilized onto nanoparticles and/or microparticles to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences. In one example, an attachment molecule can include a peptide having the amino acid sequence of SEQ ID NO: 1 that is chemically immobilized onto the nanoparticles and/or microparticles to facilitate cell attachment.

The nanoparticles and/or microparticles can also be formed from inorganic materials, such as calcium phosphate materials including mineralite, carbonated nano-apatite, calcium phosphate based mineralite, tri-calcium phosphate, octa-calcium phosphate, calcium deficient apatite, amorphous calcium phosphate, hydroxyapatite, substitute apatite, carbonated apatite-like minerals, highly substituted carbonated apatites or a mixture thereof. Calcium phosphate nanoparticles and/or microparticles can have an average particle size of between about 1 nm and about 200 µm. It will be appreciated that smaller or larger calcium phosphate nanoparticles and/or microparticles may be used. The calcium phosphate nanoparticles and/or microparticles can have a generally spherical morphology and be of a substantially uniform size or, alternatively, may be irregular in morphology. Calcium phosphate nanoparticles and/or microparticles may be complexed with surface modifying agents to provide a threshold surface energy sufficient to bind material (e.g., bioactive agents) to the surface of the microparticle without denaturing the material. Non-limiting examples of surface modifying agents can include basic or modified sugars, such as cellobiose, carbohydrates, carbohydrate derivatives, macromolecules with carbohydrate-like components characterized by an abundance of —OH side groups and polyethylene glycol.

In some embodiments, the nanoparticles and/or microparticles can include at least one, two, three, or more bioactive agent(s) that is capable of modulating a function and/or characteristic of a cell. For example, the bioactive agent may be capable of modulating a function and/or characteristic of a cell that is dispersed with the nanoparticles and/or microparticles. Alternatively or additionally, the bioactive agent may be capable of modulating a function and/or characteristic of an endogenous cell surrounding a tissue construct formed of the cell aggregate implanted in a tissue defect.

In some embodiments, the at least one bioactive agent can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, miRNAs, DNA encoding for an shRNA of interest, oligonucleotides, proteoglycans, glycoproteins, and glycosaminoglycans.

It will be appreciated at least one bioactive agent can be incorporated on or within at least one microparticle. The at least one microparticle can differentially or controllably release the at least one bioactive agent or be taken up (e.g., via endocytosis) by at least one cell to modulate the function and/or characteristic of the cell. The at least one bioactive agent may be at least partially coated on the surface of the at least one microparticle. Alternatively, the at least one bioactive agent may be dispersed, incorporated, and/or impregnated within the microparticle. For example, a bioactive agent comprising a DNA plasmid (e.g., a plasmid encoding BMP-2) can be coated onto the surface of the microparticle. After forming the nanoparticles and/or microparticles with the bioactive agent, the nanoparticles and/or microparticles can be coated with DNA or protein to prevent nanoparticle aggregation and/or promote cellular uptake. It will be appreciated that one or more of the same or different bioactive agents can be incorporated on or within the at least one nanoparticles and/or microparticles.

In some embodiments, a bioactive agent can comprise an interfering RNA or miRNA molecule incorporated on or within at least one microparticle dispersed on or within the cell aggregate. The interfering RNA or miRNA molecule can include any RNA molecule that is capable of silencing an mRNA and thereby reducing or inhibiting expression of a polypeptide encoded by the target mRNA. Alternatively, the interfering RNA molecule can include a DNA molecule encoding for an shRNA of interest. For example, the interfering RNA molecule can comprise a short interfering RNA (siRNA) or microRNA molecule capable of silencing a target mRNA that encodes any one or combination of the polypeptides or proteins described above. The at least one microparticle can differentially or controllably release the at least one interfering RNA molecule or be taken up (e.g., via endocytosis) by at least one cell to modulate a function and/or characteristic of the cell.

The type, distribution, size, and/or crosslinking of the nanoparticles and/or microparticles can also be modified or configured to differentially, controllably, spatially, and/or temporally release at least one bioactive agent in the cell aggregate. In some embodiments, individual nanoparticles and/or microparticles can be formed of different materials or components, such as different polymers having different molecular weights or cross-linking. Moreover, the nanoparticles and/or microparticles can be formed into particular shapes or form to facilitate release of one or more bioactive agents according to a specific temoral release profile. Alternatively, one or more materials or agents can be added to the nanoparticles and/or microparticles to facilitate differential and/or controlled release of one or more bioactive agents according to a temporal release profile. For example, during formation of the nanoparticles and/or microparticles, the concentration of bioactive molecules incorporated into the nanoparticles and/or microparticles can be increased or decreased to increase or decrease the concentration of the bioactive molecules upon release from the nanoparticles and/or microparticles.

In some embodiments, the cell aggregate can include a plurality of first nanoparticles and/or microparticles that can include or release one or more first bioactive agent(s) and a plurality of second nanoparticles and/or microparticles that can include or release one or more second bioactive agent(s). The one or more first bioactive agents and the one or more second bioactive agents may comprise the same or different agents. The one or more first bioactive agents and the one or more second bioactive agents can be differentially, sequentially, and/or controllably released from the first nanoparticles and/or microparticles and second nanoparticles and/or microparticles to modulate a different function and/or characteristic of a cell. It will be appreciated that the one or more first bioactive agents can have a release profile that is the same or different from the release profile of the one or more second bioactive agents from the first nanoparticles and/or microparticles and the second nanoparticles and/or microparticles. Additionally, it will be appreciated that the first nanoparticles and/or microparticles can degrade or diffuse before the degradation or diffusion of the second nanoparticles and/or microparticles or allow for an increased rate of release or diffusion of the one or more first bioactive agents compared to the release of the one or more second bioactive agents. The first and second nanoparticles and/or microparticles may be dispersed uniformly on or within the cell aggregate or, alternatively, dispersed such that different densities of the first nanoparticles and/or microparticles and second nanoparticles and/or microparticles are localized on or within different portions of the cell aggregate.

In some embodiments, the self-assembled, scaffold-free high density cell aggregate can be formed by combining the nanoparticles and/or microparticles with the cells and then suspending the cells and the nanoparticles and/or microparticles in a culture medium. The nanoparticles and/or microparticles can be formed, for example, from a hydrogel, such as gelatin, that is cross-linked with a cross-linking agent, (e.g., genipin). In some instances, the nanoparticles and/or microparticles can have a diameter of about 20 um to about 100 um and a degree of crosslinking of about 20% to about 70%. The nanoparticles and/or microparticles can also include a growth factor, such as TGFB1, that can be loaded in the nanoparticles and/or microparticles and controllably released from the nanoparticles and/or microparticles. Cell aggregates incorporated with fast degrading nanoparticles and/or microparticles containing TGF-β1 produced significantly more GAG and GAG per DNA.

The cells can include any totipotent stem cell, pluripotent stem cell, or multipotent stem cell, and/or differentiated cell. Progenitor cells can include autologous cells; however, it will be appreciated that xenogeneic, allogeneic, or syngeneic cells may also be used. The progenitor cells employed may be primary cells, expanded cells or cell lines, and may be dividing or non-dividing cells. The cells can be derived from any desired source. For example, the cells may be derived from primary tissue explants and preparations thereof, cell lines (including transformed cells) that have been passaged once (P1), twice (P2), or even more times, or host cells (e.g., human hosts). Any known method may be employed to harvest cells for use in the present invention. For example, mesenchymal stem cells, which can differentiate into a variety of mesenchymal or connective tissues (e.g., adipose tissue, osseous tissue, cartilaginous tissue, elastic tissue, and fibrous connective tissues), can be isolated according to the techniques disclosed in U.S. Pat. No. 5,486,359 to Caplan et al. and U.S. Pat. No. 5,226,914 to Caplan et al., the entireties of which are hereby incorporated by reference. In one example, the population of cells can comprise a population of human mesenchymal stem cells. In another example, the population of cells can comprise a population of human adipose derived stem cells.

The culture medium may include, for example, high-glucose DMEM supplemented with dexamethasone, ascorbate-2-phosphate, sodium pyruvate, and a premix of insulin, transferrin and selenium (ITS). By way of example, the medium may include high-glucose DMEM containing about 100 mM sodium pyruvate, about 80 µM ascorbate-2-phosphate, about 100 nM dexamethasone, and about 1% ITS. Additional medium components may include L-Glutamine, DMEM non-essential amino acid solution, and/or an antibiotic/antimycotic.

The nanoparticles and/or microparticles may be dispersed with cells in the suspension in a substantially uniform manner. The suspension can be provided in a culture vessel or chamber including but not limited to a tube, multiwall plate, transwell membrane, or bioreactor. The density at which the cells are seeded into the culture chamber can be, for example, about $1 \times 10^5$ cells/mL to about $100 \times 10^6$ cells/mL.

During culturing, the bioactive agent can be released from the nanoparticles and/or microparticles via diffusion and/or as the nanoparticles and/or microparticles begin to degrade. Controlled release of the bioactive agent from the microparticles may be dependent on the size and composition of the nanoparticles and/or microparticles, as well as the composition of the medium in which the aggregate is immersed. For example, the release rate of the bioactive agent(s) can be selectively controlled by changing the degree or percent of crosslinking of the polymers used to form the nanoparticles and/or microparticles, the size of the nanoparticles and/or microparticles, and the amount of bioactive agent that is loaded into the nanoparticles and/or microparticles.

It will be appreciated that growth factors can also be added to the medium to enhance or stimulate cell growth. Examples of growth factors include transforming growth factor-β (TGF-β) (e.g., TGF-β1 or TGF-β3), platelet-derived growth factor, insulin-like growth factor, acid fibroblast growth factor, basic fibroblast growth factor, epidermal growth factor, hepatocytic growth factor, keratinocyte growth factor, and bone morphogenic protein. It will also be appreciated that other agents, such as cytokines, hormones (e.g., parathyroid hormone, parathyroid hormone-related protein, hydrocortisone, thyroxine, insulin), fatty acids (e.g., Omega-3 fatty acids such as α18:3 linolenate), and/or vitamins (e.g., vitamin D), may also be added or removed from the serum-free medium to promote cell growth.

The cells and nanoparticles and/or microparticles can be cultured at a temperature and atmosphere effective to promote formation of high density cell aggregate. For example, the cells may be cultured at a temperature of about 37° C. in an atmosphere of about 5% carbon dioxide at an about 90% to about 95% humidity. The oxygen percentage can be varied from about 1% to about 21%. Typically, the cells can be cultured for about 1 to about 10 weeks.

The inclusion of the nanoparticles and/or microparticles in the cell aggregate can allow for substantially more uniform spatial delivery of the bioactive agent throughout the interior of the aggregate. The substantially uniform distribution of the nanoparticles and/or microparticles and relatively uniform release of the bioactive agent in the high density cell aggregate is advantageous for several reasons, including, but not limited to: (1) rapidly inducing uniform cell differentiation; (2) providing control over the spatial and temporal presentation of bioactive agents; (3) allowing for the use of lower concentrations of bioactive agents as compared to systems employing exogenously-supplied growth factors; (4) enhancing the spatial distribution of extracellular matrix that is formed between the cells; and (5) enhancing the amount of extracellular matrix produced in the cell aggregate. These enhanced properties allows and/or provides for the formation of larger, more mechanically robust cell aggregates that can subsequently be manipulated for tissue engineering applications.

It will be appreciated that the high density cell aggregate can further include other nanoparticles and/or microparticles, such as second, third, fourth, or more nanoparticles that include other (e.g., second, third, fourth, or more) bioactive agents. The other bioactive agents may be the same or different type of agent (described above). The other nanoparticles and/or microparticles can differentially, sequentially, and/or controllably release the different bioactive agents to modulate the same or different function and/or characteristics of at least one cell in the aggregate. The bioactive agents can have the same or different release profiles from the first nanoparticles and/or microparticles.

As a result of culturing the cells with the nanoparticles and/or microparticles, a mechanically robust cell aggregate can be formed that can readily shaped, transferred, and/or manipulated to form the tissue construct. In some embodiments, the cell aggregate can comprise a single layer or sheet of tissue differentiated or substantially differentiated cells that are dispersed within an endogenously produced extracellular matrix with the completely or partially degraded microspheres. In some embodiments, the cell aggregate can comprise a sheet of cartilage tissue with a glycosaminoglycan (GAG) content that can be substantially equal to the GAG content of native cartilage. In other embodiments, the cell aggregate can be in a spheroid or oblate spheroid shape. The shape of the cell aggregate is not limited can vary depending on the culture vessel utilized and the culturing conditions.

The cell aggregate (e.g., sheet of tissue) can be harvested from the by, for example, lifting the layer of cell aggregate out of the culture chamber. The cell aggregate so formed can be shaped, molded, or configured into a variety of tissue constructs that can be used in a various biomedical applications, including tissue engineering, drug discovery applications, and regenerative medicine. In one example, a tissue construct comprising the cell aggregate can be used to promote tissue growth in a subject by administering the tissue construct to a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the tissue construct can be administered to the target site by, for example, implantation into the tissue defect. Prior to implantation, the tissue construct comprising the cell aggregate can be formed into the shape of the tissue defect using tactile means. Alternatively, the tissue construct may be formed into a specific shape prior to implantation into the subject.

The tissue construct may be attached to the target site using, for example, adhesive materials, such as bioadhesives, sutures, staples, and/or a membrane covering. Examples of adhesive materials include calcium phosphate-based pastes (e.g., αBMM), fibrin-based glues, transglutaminase, and chemical cross-linking agents (e.g., 1-ethyl-3-[3-dimethylaminopropyl]carbodiimide hydrochloride).

After injecting implanting the tissue construct into the subject, the cells of the tissue construct can express growth and/or differentiation factors, and/or promote progenitor cell expansion and differentiation. Additionally, the presence of the tissue construct in the tissue defect may promote migration of endogenous cells surrounding the tissue defect into the tissue construct. Moreover, the tissue construct can secrete factors that affect surrounding cells in a trophic manner. This can act to improve healing/regeneration, immunomodulate or treat disease states.

Figure 14:
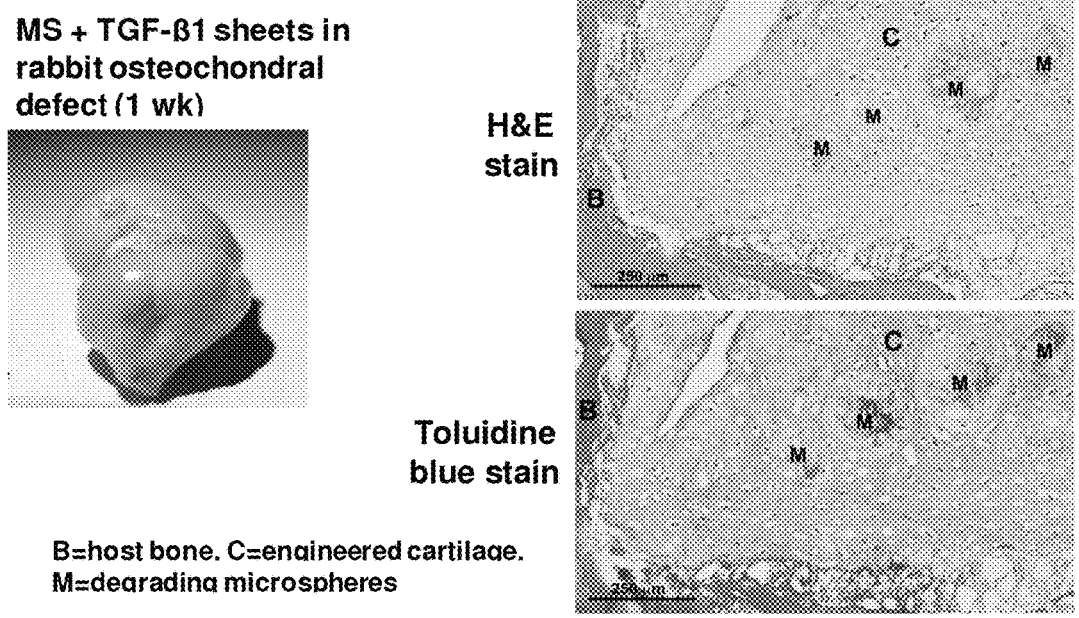
FIG. 14 illustrates images showing cell sheet incorporating microspheres and TGF-β1 provided in a rabbit osteochondral defect.
Figure 15:
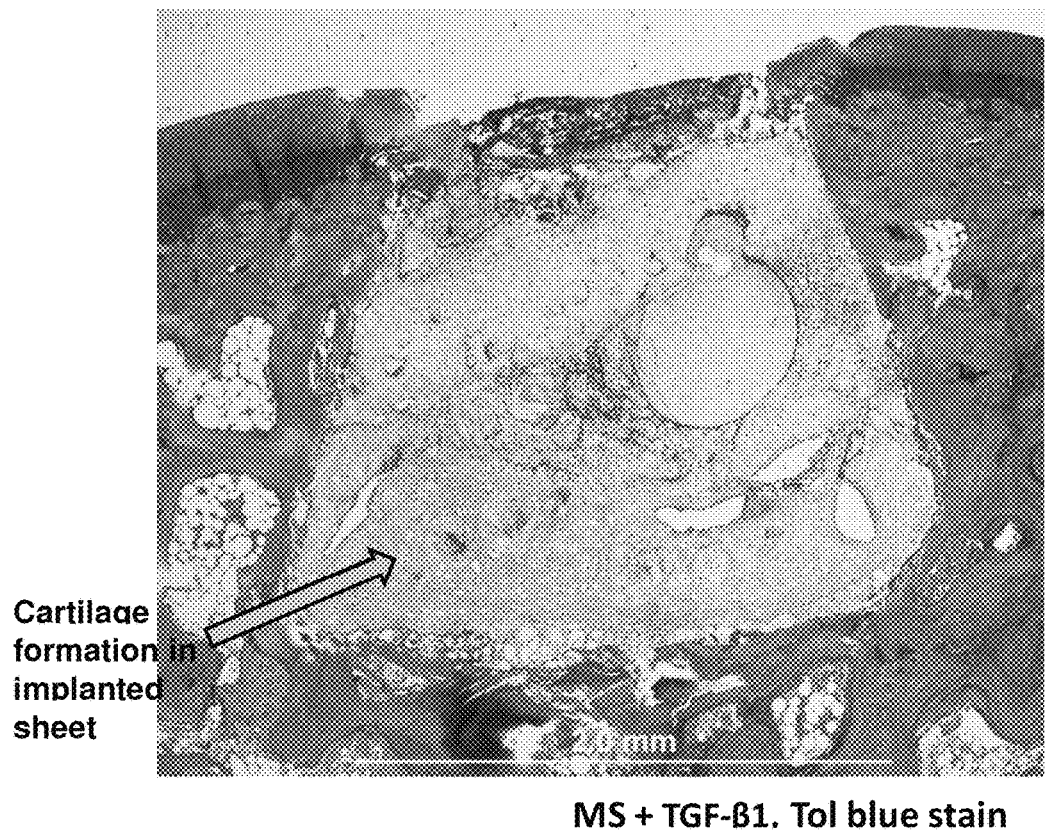
FIG. 15 illustrates an image showing cartilage integration in the implanted sheet of FIG. 14 provided in osteochondral defect of the rabbit.

By way of example, FIG. 14 illustrates images showing a tissue construct comprising a cell sheet incorporating microspheres and TGF-β1 that can be administered to treat a rabbit osteochondral defect. FIG. 15 shows that native cartilage can readily integrate into the tissue construct to treat the osteochondral defect of the rabbit.

In other embodiments, a heterogenous cell aggregate or tissue construct can be formed that includes defined regions or portion (e.g., layers) of differing or similar cell aggregate materials. The differing regions or portions of the heterogenous cell aggregate or tissue construct can be provided or formed with or without nanoparticles and/or microparticles and can have similar or different properties to vary the properties of the tissue construct for particular tissue engineering applications.

In some embodiments, a heterogenous cell aggregate can be formed by seeding a first mixture of nanopaticles and/or microparticles and cells in a culture chamber and then seeding at least a second mixture of cells nanoparticles and/or microparticles over, around, within, and/or along select portions of the seeded first mixture of nanopaticles and/or microparticles and cells. The first mixture of nanopaticles and/or microparticles and cells can include the same or different type, concentration, amount, and/or distribution, of cells, nanoparticles and/or microparticles and/or potentially bioactive agents as the second mixture of nanopaticles and/or microparticles and cells to vary the compositions and properties of the tissue construct for particular tissue engineering applications. It will be appreciated that the first mixture and/or second mixture may be free of cells. For example, a heterogenous cell aggregate can be formed by seeding a first mixture of nanopaticles and/or microparticles and cells in a culture chamber and then seeding a mixture of cells that is free of the nanoparticles and/or microparticles over, around, within, and/or along select portions of the seeded first mixture of nanopaticles and/or microparticles and cells.

In other embodiments, a heterogenous cell aggregate or tissue construct that includes defined regions or portion (e.g., layers) of differing materials can be formed by layering portions or sheets of cell aggregates described herein can layered to from a heterogenous or multilayer tissue construct. For example, a first portion of a sheet of cell aggregate may be folded over onto a second portion of the sheet. An optional load, such as a compressive, load can then be applied to the folded construct for an amount of time (e.g., about 1 week) effective to promote integration of the layers.

The multilayer cartilage tissue construct so formed may be removed from the culture vessel and applied to an articular surface. Additionally, it should be appreciated that the thickness of the multilayer cartilage tissue construct may be adjusted as needed by adding or removing layers. For example, a plurality of layers may be sandwiched, adhered, or mechanically manipulated by, for example, compression, tension, hydrostatic loading, or shear loading, and formed into a multilayer cartilage tissue construct having a thickness of about 1 mm to about 4 mm or greater.

Figure 16:
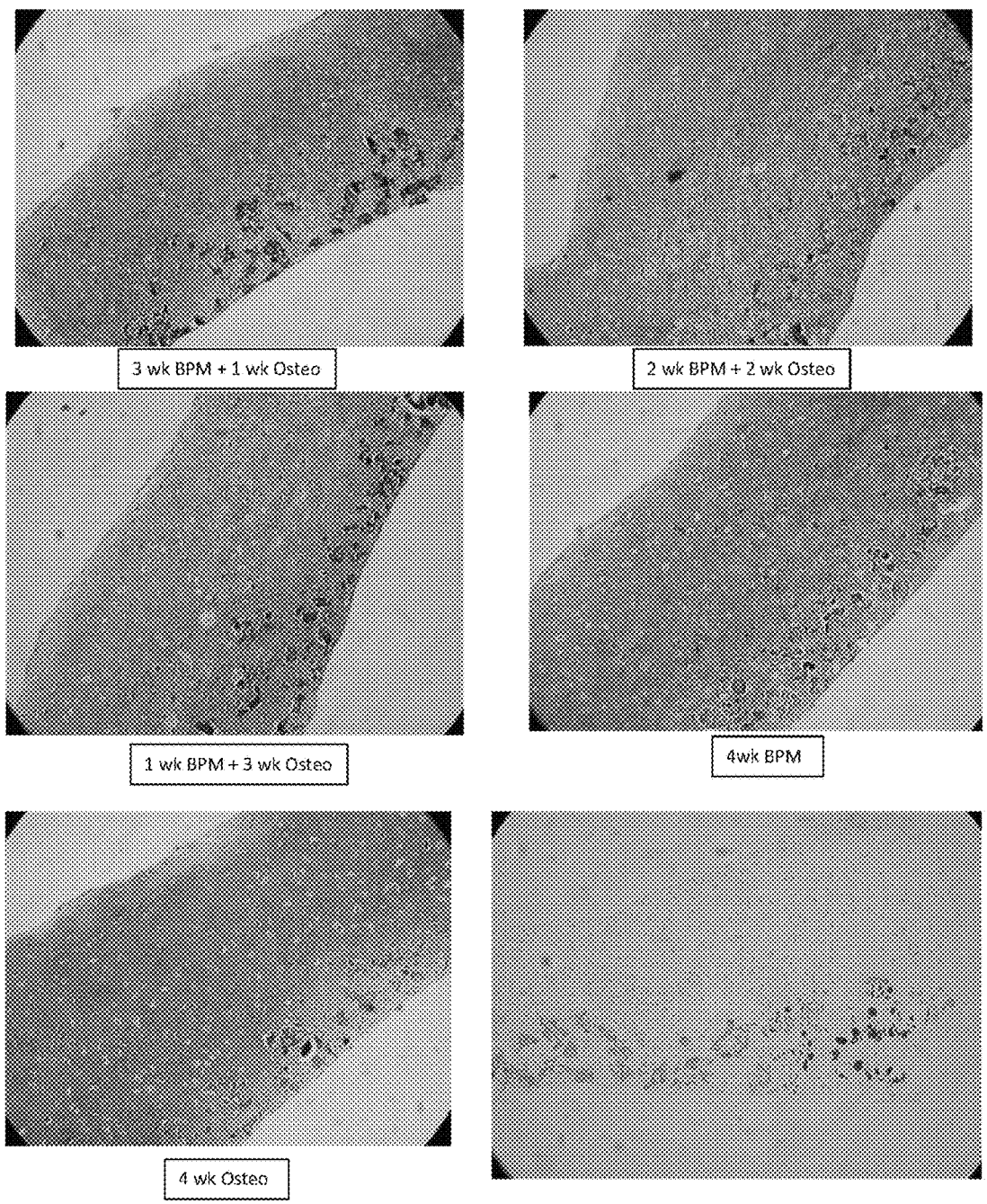
FIG. 16 illustrates images of the histology of a bilayer osteochondral tissue construct in accordance with an embodiment described herein.
Figure 17:
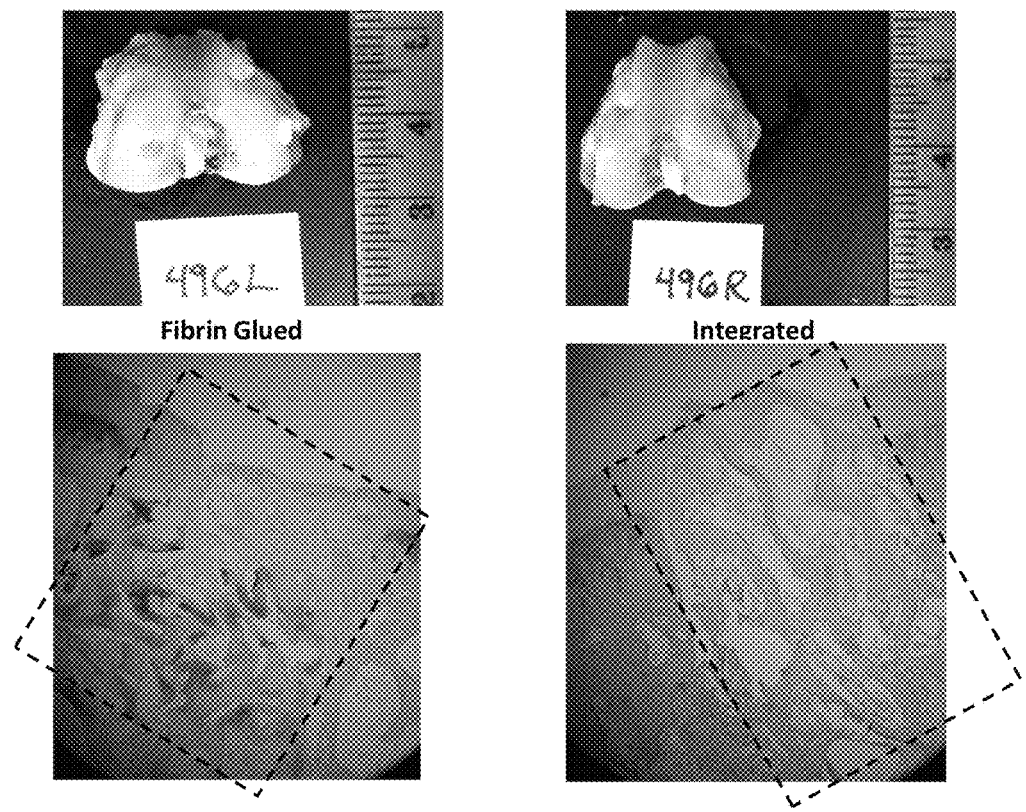
FIG. 17 illustrates a schematic image of a tissue construct comprising a cell sheet with integrated demineralized bone matrix provided in a rabbit osteochondral defect.

In another method, at least two tissue constructs can formed from similar and/or substantially different cell aggregates may be layered on one another and then allowed to integrate or adhere and/or mechanically manipulated, by, for example, compression, tension, hydrostatic loading, or shear loading. For example, as shown in FIGS. 16 and 17, at least two sheets or layers of the cell aggregate can be adhered and shaped to a configuration or shape of a osteochondral defect and then administered to the osteochondral defect. FIG. 17 shows the multilayer tissue construct can be readily implanted and integrated osteochondral defect.

Figure 18:
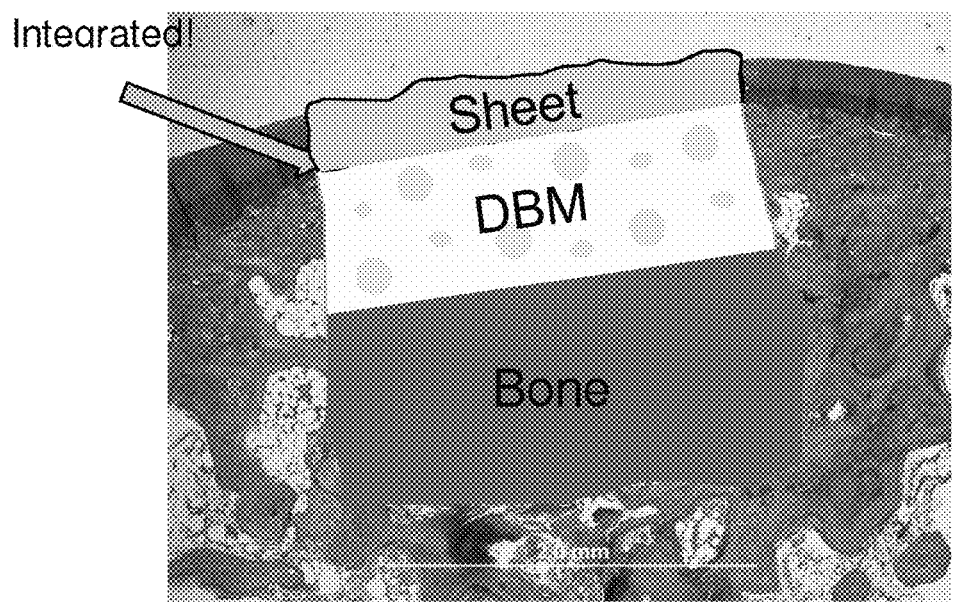
FIG. 18 illustrates photographs of a tissue construct comprising a cell sheet with integrated demineralized bone matrix and a photograph of the tissue construct provided in a rabbit osteochondral defect
Figure 19:
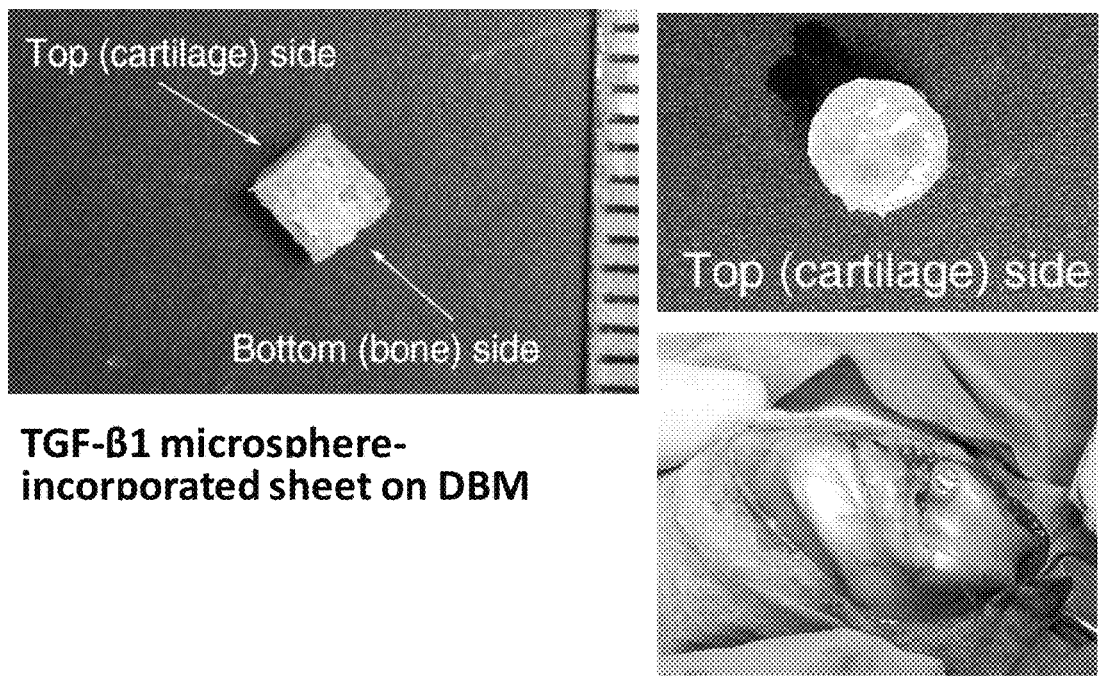
FIG. 19 illustrates photographs showing the histology of the tissue construct of FIG. 18 after 2 weeks in a rabbit osteochondral defect.

In still other embodiments, the cell aggregates described herein can be combined with or adhered to other tissue constructs to form a heterogenous tissue construct. For example, as shown in FIGS. 18 and 19, a sheet of the cell aggregate can be provided on, combined with or adhered to demineralized bone matrix to provide and osteochondral tissue construct. As shown in FIG. 20, the tissue construct can be readily implanted and integrated osteochondral defect.

In other embodiments, the DNA or cells in the cell aggregate can be removed or lysed to provide an acellular tissue construct that includes the extracellular matrix so formed and, potentially, the partially or completely degraded nanoparticles and/or microparticles. Removal may be achieved by, for example, detergent treatment, (e.g., SDS treatment) treatment with DNase and RNase, and/or freeze/thaw cycles. The acellular tissue construct can then be used alone for tissue engineering application or in combination with other cell types or growth factors for the promotion of tissue repair. The acellular tissue construct can be used as an acellular biomaterial for tissue engineering application similar to the above after decellularization. When used alone, the acellular tissue can be used to prevent or repair tissue defects, enhance host cell attachment, infiltration, differentiation, extension, and proliferation. The acellular tissue construct as a decellularized product can be used together with other known bioactive agents and cell types for the promotion of tissue repair.

The following examples are for the purpose of illustration only and are not intended to limit the scope of the claims, which are appended hereto.

Example 1

In this Example, we describe a system of self-assembled, microsphere incorporated human MSC (hMSC) sheets capable of forming cartilage in the presence of exogenous TGF-β1 or with TGF-β1 released from the incorporated microspheres. Our hypothesis was that the incorporation of gelatin microspheres with or without growth factor into hMSC sheets could improve both the mechanical properties and spatial distribution of neocartilage matrix. We also hypothesized that TGF-β1 loaded microspheres could enable enhanced chondrogenesis in hMSC sheets without requiring exogenous growth factor supplementation. Gelatin microspheres with two different degrees of genipin crosslinking enabled elucidation of the roles of different microsphere degradation and growth factor release rates on chondrogenesis within the system.

Materials and Methods
hMSC Isolation and Culture

Bone marrow aspirates from the posterior iliac crest of healthy donors were obtained under a protocol approved by the University Hospitals of Cleveland Institutional Review Board and processed by the Skeletal Research Center Mesenchymal Stem Cell Core Facility as previously described. Briefly, the aspirates were washed with growth medium, which was comprised of low glucose Dulbecco's modified Eagle's medium (DMEM-LG; Sigma) containing 10% pre-screened fetal bovine serum (FBS). Mononucleated cells were isolated via centrifugation with a Percoll (Sigma) density gradient. Isolated cells were seeded at a density of $1.8 \times 10^5$ cells/cm$^2$ in growth medium and cultured at 37° C. with 5% $CO_2$ in a humidified incubator. After 4 days, nonadherent cells were removed by a medium change. Subsequently, medium was changed every 3 days. After approximately 2 weeks, primary cultures were subcultured and plated at $5 \times 10^3$ cells/cm$^2$. Cells were used at passage 2 or 3.

Gelatin Microsphere Synthesis

Gelatin microspheres were synthesized according to a previously established method with slight modifications. All chemicals used in these studies were from Fisher Chemical unless otherwise noted. Briefly, an aqueous solution of 11.1 wt. % acidic gelatin (Sigma) was preheated to 45° C., added dropwise into 250 ml of olive oil (Gia Russa) at 45° C. and stirred at 500 RPM for 10 min. The solution temperature was lowered to 4° C. with constant stirring to facilitate gelation. After 30 min, 100 ml chilled acetone (4° C.) was added to the stirring solution. After 1 h, an additional 100 ml of acetone was added to the emulsion and stirred for 5 min at 1000 RPM. The resulting microspheres were collected by filtration, washed with acetone to remove residual olive oil, and air dried. Dry microspheres were crosslinked at room temperature in an aqueous solution of 1 wt. % genipin ("Gp"; Wako USA) for either 2 h ("low Gp") or 21 h ("high Gp") to produce microspheres with different crosslinking densities. Genipin covalently binds primary amine residues on the gelatin, forming intramolecular and short-range intermolecular crosslinks. Crosslinked microspheres were collected by filtration, washed 3 times with ultrapure deionized water (diH$_2$O), and lyophilized Growth factor-loaded microspheres were prepared by soaking crosslinked microspheres in a solution of TGF-β1 (Peprotech) in phosphate buffered saline (PBS) at pH 7.4 for 2 h at 37° C. At pH 7.4, complexation occurs between positively charged TGF-β1 (IEP of 9.5) and acidic gelatin (IEP of 5.0). To ensure complete absorption during loading, the volume of TGF-β1 solution added was much less than the equilibrium swelling volume of the microspheres. Unloaded microspheres without growth factor were hydrated similarly with PBS.

Microsphere Characterization

Hydrated microspheres were imaged via light microscopy on a TMS microscope (Nikon) with a Coolpix995 camera (Nikon) and their diameters were measured using Image J analysis software (N=245, "low Gp"; N=230, "high Gp"). Microsphere crosslinking densities were determined by a ninhydrin assay as previously described. Briefly, 3 mg microspheres were hydrated in 100 μl diH2O and 1 ml of a ninhydrin solution (1.05 g citric acid, 0.4 g NaOH, 0.04 g SnCl.2H2O, 1 g ninhydrin, 25 ml 2-methoxyethanol, and 25 ml diH$_2$O) was added (N=4). Samples and glycine standards were incubated at 100° C. for 20 min, 5 ml of 50% isopropanol was added to each, and 200 μl aliquots were added to the wells of a 96-well plate. The absorbance was read at 570 nm on a Safire microplate reader (Tecan, Durham, N.C.). The concentration of free amino groups was determined by comparison to glycine standards. Degree of crosslinking was defined as the percentage of free amino groups within gelatin microspheres that were reacted with the crosslinking agent.

To determine growth factor release from crosslinked microspheres in cell culture media without proteases, microspheres were loaded with 100 ng TGF-β1 per mg and suspended in a concentration of 5 mg of microspheres per 1 ml of DMEM-LG. One ml samples of the suspensions were added to microcentrifuge tubes, and then the tubes were placed on a rotary shaker at 40 RPM and 37° C. (N=4). At various points over a period of 16 days, samples were centrifuged, the supernatant was collected, and fresh release medium was added. TGF-β1 release was quantified using an ELISA kit (R&D Systems). To determine microsphere degradation rates in protease-containing media, microspheres were hydrated in PBS then suspended at a concentration of 5 mg/ml in PBS containing 10 ng/ml Type II Collagenase (Worthington) and incubated at 37° C. (N=3). The buffer solution was changed every 3-4 days in all samples. At days 0, 1, 4, 8, 14, and 21, microsphere samples were collected via centrifugation and the supernatant was discarded. The microsphere samples were frozen and lyophilized to dryness, and weighed to determine mass loss over time.

Microsphere-Incorporated hMSC Sheet Production

Crosslinked microspheres were UV sterilized for 10 min, then soaked with PBS or loaded with 400 ng TGF-β1 per mg microspheres. 1.5 mg microspheres with or without TGF-β1 were combined with $2 \times 10^6$ hMSCs and suspended in 500 μl of a 1:1 mixture of growth medium and chemically defined medium (DMEM-HG with 1% ITS+Premix (BD Biosciences), 37.5 μg/ml ascorbate-2-phosphate (Wako USA), 10-7 M dexamethasone (MP Biomedicals), 1% nonessential amino acids (HyClone), and 1% sodium pyruvate (HyClone)) and allowed to settle onto the membranes of 12 mm Transwell inserts (Corning) for 48 h in a humidified incubator at 37° C. with 5% $CO_2$. Control sheets without microspheres were also prepared. 10 ng/ml TGF-β1 was added only to the media of control sheets without microspheres and sheets containing unloaded microspheres. After 48 h, the media was replaced with 2.5 ml chemically defined media, and subsequently changed every other day with TGF-β1 supplemented in the specified conditions. Negative control sheets incorporated with unloaded microspheres were also prepared and cultured in media without growth factor.

Sheet Harvest and Biochemical Analysis

Sheets were harvested for analysis after 3 weeks in culture and their wet masses were determined. Two 5 mm-diameter punches were taken from each sheet for DNA and glycosaminoglycan (GAG) quantification (N=4) or frozen for subsequent thickness measurements and mechanical testing (N≥3). Remaining sheet portions were processed for immunohistologic evaluation (N=4). Punches designated for biochemical analysis were digested with papain (Sigma) at 65° C. for 2-3 h, and the digests were assayed for DNA and GAG content with PicoGreen (Invitrogen) and dimethylmethylene blue (DMMB) dye (Sigma), respectively.

Histology and Immunohistochemistry (IHC)

Portions of the sheets designated for immunohistological analysis were fixed in formalin and paraffin-embedded. 5 μm sections were stained for GAG content via Safranin O (Acros Organics) with a Fast Green counterstain or type I and II collagen as previously described. Briefly, sections designated for IHC were deparaffinized, pronase-digested, and blocked with 5% BSA. Primary antibodies anti-Collagen Type I (Col-1, Sigma) and anti-Collagen Type II (Cat# II-II6B3, Developmental Studies Hybridoma Bank) or control mouse IgG (Vector Laboratories) were applied to adjacent sections. FITC conjugated goat anti-Mouse IgG (MP Biomedicals) was used as the secondary antibody. Hoechst 33258 (Sigma) was used as a nuclear counterstain. Slides were mounted with Fluoromount (Sigma) and imaged using an Axio Observer Z1 (Zeiss) inverted fluorescent microscope equipped with a C10600 digital camera (Hamamatsu).

Mechanical Testing

Step strain stress-relaxation testing in unconfined compression was performed using a computer-controlled testing system (Test Resources, Shakopee, Minn., USA) with modifications to a previously described protocol. Prior to mechanical testing, frozen 5 mm diameter sheet punches were thawed and equilibrated in PBS for 2 h at room temperature, and thickness measurements were taken with a micrometer. Samples were immersed in PBS, where they remained throughout the testing process. Three sequential 5% step strains were applied to the specimens with a ramp displacement rate of 0.001 mm/s. Each ramp displacement was held until the measured reaction force reached equilibrium, which was defined as a force change of less than 0.005 N in 250 s. Equilibrium stress-strain curves were generated based on the magnitude of the equilibrium forces measured after each step strain. An equilibrium compressive modulus (E) value for each sample was obtained from the slope of the equilibrium stress-strain curve, which was considered linear for strains below 15%.

Statistical Analysis

All values are reported as mean±standard deviation. Statistical analyses were performed on all groups using one-way ANOVA with Tukey's post hoc tests, except for microsphere diameters which were compared via a nonparametric Mann-Whitney test. Statistical analyses were performed using GraphPad InStat 3.06 software, with values of pb0.05 considered statistically significant.

Results

Microsphere Characterization

Figure 2:
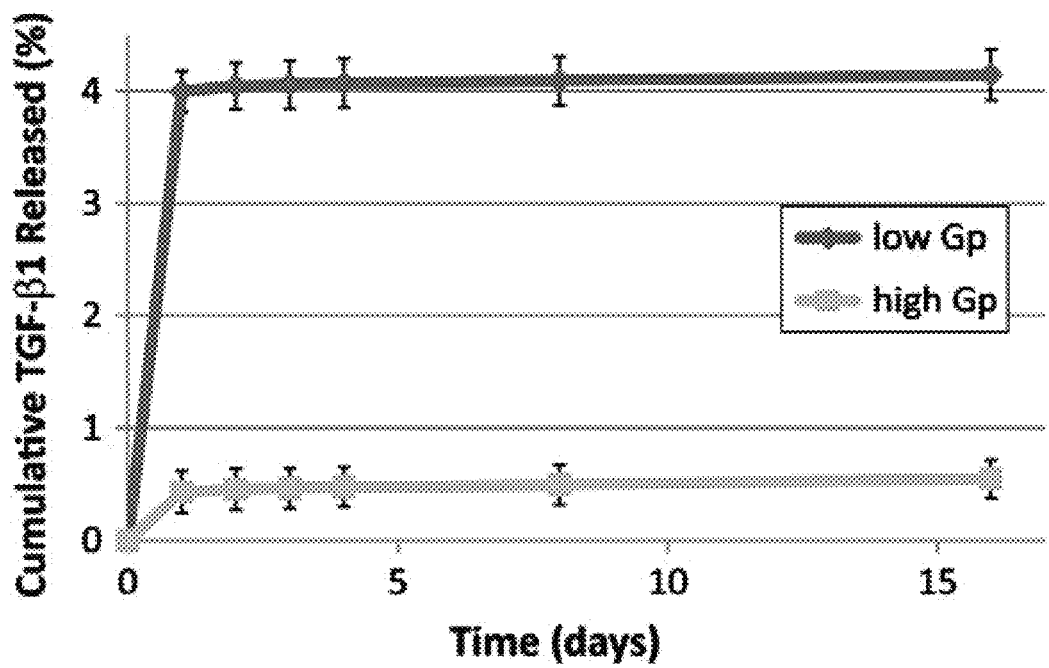
FIG. 2 illustrates diffusion-mediated release of TGF-β1 from both formulations of microspheres in non-protease containing media.
Figure 3:
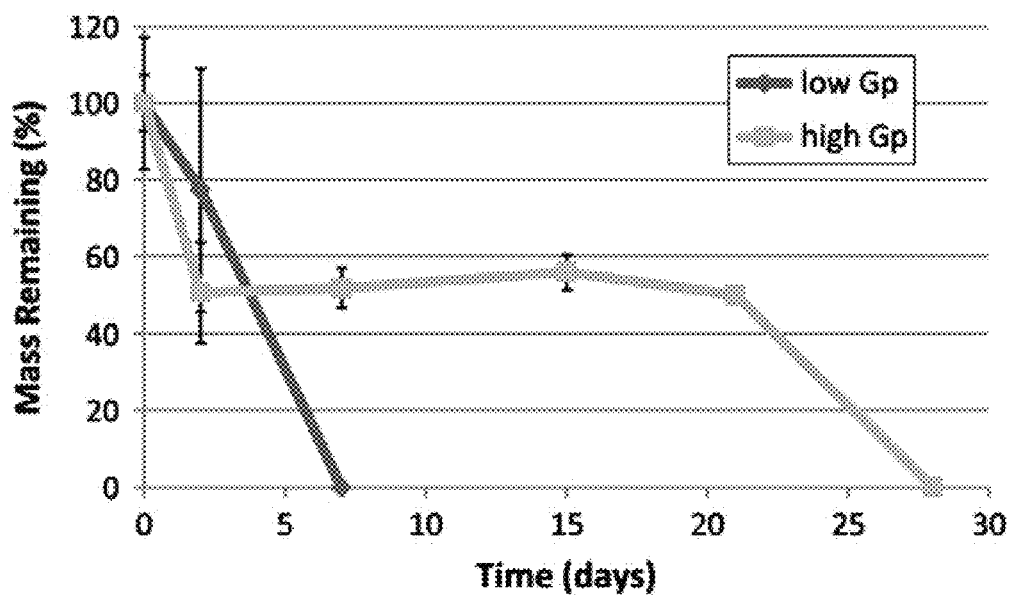
FIG. 3 illustrates mass loss over time from high Gp and low Gp microspheres in collagenase containing media.

Hydrated gelatin microspheres were roughly spherical, with smooth surfaces (FIG. 1). The diameters of low and high Gp microspheres did not significantly differ, while the degrees of crosslinking between microsphere groups were significantly different, with the low Gp group 28.3±7.2% crosslinked and the high Gp group 67.6±4.5% crosslinked (Table 1). High Gp microspheres were a dark blue color as a result of the genipin crosslinking reaction. Growth factor release from crosslinked microspheres was measured over 16 days in DMEM (FIG. 2). By day 16, only a small fraction of the total incorporated TGF-β1 was released from the microspheres, with 4.14±0.23% release from low Gp and 0.55±0.17% release from high Gp. From previous reports, it is likely that most of the incorporated TGF-β1 remained entrapped within the microspheres, retained via charge interactions. In protease-containing media, low Gp microspheres degraded more quickly, and were completely degraded after 7 days (FIG. 3). High Gp microspheres degraded more slowly, with a remaining undegraded mass of 50.0±0.1% after 3 weeks.

Harvest of Microsphere-Incorporated hMSC Sheets

After 3 weeks of in vitro culture, sheets were easily harvested by peeling from Transwell membranes and photographed (FIGS. 4A-E). Sets of sheets cultured in media supplemented with exogenous TGF-β1 containing hMSCs only, unloaded low Gp microspheres, or unloaded high Gp microspheres were designated control, low Gp+exo., and high Gp+exo., respectively. Sheets cultured without exogenous growth factor containing low Gp microspheres loaded with TGF-β1 or high Gp microspheres loaded with TGF-β1 were designated low Gp+TGF-β1, and high Gp+TGF-β1, respectively. The dark blue color in FIGS. 4C and E is due to the presence of undegraded high Gp microspheres. All sheets initially incorporated with microspheres had significantly greater wet masses than the control sheets, but there were no significant differences among the microsphere containing sheets (FIG. 5A). Negative control sheets incorporated with unloaded microspheres and cultured in media without TGF-β1 were originally prepared, but they did not undergo chondrogenic differentiation due to lack of necessary growth factor supplementation in the serum-free media. As a result, these negative controls did not survive the 3 week culture period and were not available for histologic, biochemical, or mechanical analyses.

DNA and GAG Analysis

DNA content among all conditions did not significantly differ, indicating that the presence of microspheres did not affect cell viability or proliferation after 3 weeks (FIG. 5B). Total GAG content in the low Gp+TGF-β1 group was significantly higher than that of the control and all other experimental groups (FIG. 5C), but no other significant differences in total GAG content were found. The GAG per DNA in the low Gp+TGF-β1 group was significantly higher than that of all other conditions (FIG. 5D). Additionally, both the control and low Gp+exo. groups had significantly higher GAG per DNA than the high Gp+exo. group.

Average diameters and degrees of crosslinking of the 2 formulations of microspheres

| Microsphere type | Diameter (μm) | Degree of crosslinking (%) |
| --- | --- | --- |
| Low Gp | 61.6 ± 56.0 | 28.3 ± 7.2 |
| High Gp | 53.0 ± 46.7 | 67.6 ± 4.5 |

* p < 0.001

Safranin O/Fast Green Histology

Histological sections were stained with Safranin O to indicate the presence and distribution of GAG in the center (FIG. 6A-E) and edge (6F-J) regions of sheets after 3 weeks. Dark blue high Gp microspheres are indicated by black arrows in the high Gp+exo. (FIG. 6C, H) and high Gp+TGF-β1 (FIG. 6E, J) sections. High Gp microspheres appeared to be in the process of degrading. Black arrows in the low Gp+exo. (FIG. 6B, G) and low Gp+TGF-β1 (FIG. 6D, I) sections indicate areas that appear to have been occupied by low Gp microspheres which subsequently degraded. These areas had vague circular outlines and were filled in by cells and GAG-containing matrix.

Control sheets appeared thinner than all other groups of sheets initially incorporated with microspheres. While the control sheets were thinner in the central region than at the peripheral edge, sheets from the microsphere-incorporated groups had a more uniform thickness throughout the diameter of the constructs. Additionally, the microsphere-incorporated sheets displayed more uniform GAG production throughout the thickness of each construct. This was particularly noticeable in the central region of control sheets (FIG. 6A), where there was a clear gradient from intense orange stain on the side of the sheet cultured in contact with the Transwell membrane to counterstained fibrous tissue on the opposite surface. Though there was some fibrous tissue present in the microsphereincorporated groups, they did not exhibit an obvious gradient of GAG production. This may have been due to increased nutrient diffusion within the tissues incorporated with gelatin microspheres. The low Gp+TGF-β1 sheets displayed more uniformly intense GAG staining than all other groups (FIG. 6D, I). Morphologically, neocartilage produced in the low Gp+TGF-β1 group appeared most similar to native articular cartilage, with relatively low cell density, rounded chondrocyte morphology, and large amounts of GAG-containing matrix.

Collagen Immunostaining

Histological sections were stained for type I and II collagen to determine relative amounts and distribution of collagen within the sheets (FIG. 7). It was noted that both high Gp microsphere containing groups contained degrading microspheres (FIG. 7C, E, H, J), which appear bright green due to autofluorescence of the crosslinked gelatin. Sheets from all 5 conditions were weakly positive for type I collagen, with the most intense staining visible in the control group (FIG. 7A). Type II collagen staining was weakly positive in the control group (FIG. 7F) and both groups incorporated with unloaded microspheres (FIG. 7G, H). The most intense type II collagen staining was observed in the low Gp+TGF-β1 group.

Thickness Measurements and Mechanical Testing

When measured via micrometer, all sheets initially incorporated with microspheres were significantly thicker than control sheets after 3 weeks (Table 2), which was in agreement with the histological findings. The low Gp+TGF-β1 group was significantly thicker than both the control group and the unloaded microsphere groups. In step strain stress-relaxation testing, equilibrium compressive moduli (E) for control samples could not be determined because there was no detectable change in equilibrium force with each sequential strain up to 15% strain. All groups initially incorporated with microspheres demonstrated measurable E values (Table 2). Among experimental groups, low Gp+TGF-β1 sheets had a significantly higher modulus than the low Gp+exo. group. This was the only significant difference among the microsphere-incorporated groups. These results reflected our observations, as the low Gp+TGF-β1 sheets were more firm and resistant to deformation during handling than all of the other groups, while control sheets appeared thin and fragile by comparison to all microsphere-incorporated sheets.

Thickness measurements of sheet punches and equilibrium compressive moduli from strep strain stress-relaxation testing.

| Condition | Thickness (μm) | E (kPa) |
| --- | --- | --- |
| Control | 269 ± 21[a] | — |
| Low Gp + exo. | 371 ± 41 | 1.46 ± 1.91 |
| High Gp + exo. | 366 ± 18 | 4.21 ± 2.58 |
| Low Gp + TGF-β1 | 443 ± 35[b] | 9.88 ± 6.47 |
| High Gp + TGF-β1 | 367 ± 30 | 3.52 ± 1.76 |

[a]Indicates thickness less than all other groups.
[b]Indicates thickness significantly greater than control, low Gp + exo., and high Gp + exo.
[c] Indicates E significantly greater than low Gp + exo.

Discussion

The aim of this study was to engineer self-assembling hMSC constructs containing biodegradable microspheres with or without chondrogenic growth factor, enabling improved neocartilage matrix formation and mechanical properties without requiring exogenous growth factor supplementation. In contrast to our previous work involving hMSC aggregates incorporated with TGF-β1 releasing PLGA microspheres, this system of gelatin microsphere-incorporated sheets enables the formation of larger constructs with increased GAG production and the potential for greater utility for the treatment of cartilage defects. Within this system, genipin was used as the microsphere crosslinking agent as it is less cytotoxic than the more commonly used crosslinker glutaraldehyde. Although the mean diameters of the 2 crosslinked microsphere formulations did not differ significantly, the microspheres had a wide, non-Gaussian size distribution. This is thought to be a result of the microsphere formation process, which employed a single-emulsion stirring technique.

As has been previously demonstrated, basic growth factors ionically immobilized in an acidic gelatin hydrogel can only be released by biodegradation of the hydrogel matrix, and their release is highly correlated with cell-mediated polymer degradation. Gelatin does not undergo hydrolytic degradation, so as a result, gelatin microspheres are not degraded under in vitro conditions without the presence of proteases. As expected, microspheres in non-protease containing media exhibit a small burst release, followed by very little further TGF-$\beta$1 release over a period of 16 days (FIG. 2). The initial growth factor burst is thought to be due to uncomplexed TGF-$\beta$1 molecules on the microsphere surface. Total burst release from the high Gp microspheres was less than that from the low Gp microspheres, as has been reported in other studies.

Microsphere degradation behavior was examined in collagenase containing medium (FIG. 3) to demonstrate the differences in degradation rates resulting from varied microsphere crosslinking densities under specific proteolytic conditions. A concentration of 10 ng/ml type II collagenase was selected to achieve degradation rates that roughly approximated those observed in the cellular sheets. Microspheres degraded over time at rates dependent on the level of crosslinking. At the selected protease concentration, microsphere degradation behavior was comparable to that observed in the histological images, which indicated that the low Gp microspheres within hMSC sheets were completely degraded after 3 weeks and the high Gp microspheres were only partially degraded, with many microspheres still visibly present (FIG. 6). It is important to note, however, that the selected collagenase type and concentration only approximated the microsphere degradation rate. Release of growth factors from gelatin microspheres is dependent on both protease concentration and type, and multiple protease concentrations and types could be present in the microenvironment within the microsphereincorporated cell sheets. Therefore, an accurate representation of cell mediated TGF-$\beta$1 release is difficult to obtain. TGF-$\beta$1 released from microspheres caused chondrogenic differentiation comparable to exogenous supplementation indicating that the growth factor released via cell-mediated polymer degradation was bioactive.

One of the hypotheses of this study was that the inclusion of biodegradable microspheres within neocartilage sheets could improve the spatial distribution of ECM. After 3 weeks, all sheets initially incorporated with microspheres were thicker than cell-only control sheets (FIG. 5A). This was also true in the low Gp microsphereincorporated groups, in which the gelatin microspheres were completely degraded by the time of harvest. This suggests that the incorporated microsphere volume was not solely responsible for the observed increase in thickness, but instead the degrading microspheres may have acted as spacing elements within the neocartilage tissue, allowing room for cell migration and matrix elaboration in spaces where the hydrogel degraded. This theory is supported by the biochemical and immunohistochemical results (FIG. 7), particularly in the examination of the low Gp+exo. group. The low Gp+exo. sheets had GAG and GAG/DNA levels equivalent to control sheets without microspheres, and both groups exhibited similar staining for type II collagen. However, the low Gp+exo. sheets were thicker, had a higher wet mass, and had a lower cell density as was evident in the histological images by comparison to the control. This spacing effect was not observed in the high Gp+exo. group, which contained microspheres that degraded more gradually. The high Gp+exo. Sheets had significantly less GAG per DNA than the other groups supplied with exogenous TGF-$\beta$1 (control and low Gp+exo.). While the exact cause of this result is unclear, it could be due to less room for GAG-containing matrix deposition in sheets containing slow degrading microspheres.

Since the release of ionically complexed growth factor from gelatin hydrogels is governed by hydrogel biodegradation, microspheres with a faster degradation rate could deliver more growth factor to the surrounding cells during the time course of this investigation, potentially improving chondrogenic differentiation. This appeared to be the case for the low Gp+TGF-$\beta$1 sheets. The low Gp+TGF-$\beta$1 sheets were thicker than the control group and both groups of sheets containing unloaded microspheres. Additionally, they had significantly more GAG and GAG per DNA than any of the other experimental conditions, and they stained more strongly for type II collagen. This was likely due to the fact that hMSCs within the low Gp+TGF-$\beta$1 sheets had access to more growth factor, as the microspheres underwent more cell-mediated degradation than those in the High Gp+TGF-$\beta$1 sheets. Negative control sheets incorporated with unloaded microspheres cultured in media without TGF-$\beta$1 did not undergo differentiation and fell apart during the 3 week culture period. This indicated that the cartilage formation observed in groups incorporated with growth factor loaded microspheres was not due to the incorporated microspheres themselves, but due to bioactive growth factor released from the microspheres.

Microspheres incorporated within low Gp+TGF-$\beta$1 sheets contained a total of 600 ng of incorporated growth factor, which is roughly twice the amount of total growth factor supplied to the exogenously treated sheet groups over 3 weeks. As the low Gp+TGF-$\beta$1 microspheres rapidly degraded, presumably all of the entrapped growth factor became available to the surrounding cells. High Gp+TGF-$\beta$1 microspheres were only partially degraded after 3 weeks, so the total amount of incorporated growth factor was not released from those microspheres. If only a fraction of the total incorporated growth factor was released from the partially degraded high Gp+TGF-$\beta$1 microspheres, the surrounding cells may have had access to an amount of TGF-$\beta$1 comparable to that supplied to the sheets treated with exogenous growth factor over the first 3 weeks of culture. The GAG numbers reflected this pattern, as the low Gp+TGF-$\beta$1 group had significantly more GAG and GAG per DNA than exogenously treated groups while the high Gp+TGF-$\beta$1 group had equivalent GAG and GAG per DNA to exogenously treated groups. In addition to the total growth factor concentration, the temporal profile of delivery may also have an effect on chondrogenic differentiation. Within this study, it appears that the rapid delivery of growth factor by the low Gp+TGF-$\beta$1 microspheres over the course of the first 3 weeks had a positive effect on chondrogenesis. However, the more sustained growth factor delivery from the degrading high Gp+TGF-$\beta$1 microspheres could potentially induce improved chondrogenic differentiation at later time points.

Tissue engineered hMSC sheets were subjected to step strain stress-relaxation tests in unconfined compression, as this is a method commonly used for the biomechanical characterization of tissue engineered cartilage. The thin, easily compressed control sheets exhibited changes in equilibrium force below the threshold detectable using our mechanical testing apparatus, potentially due to limited elastic matrix within these tissues. All microsphereincorporated sheets had improved mechanical properties by comparison to control sheets. This was true for low Gp-incorporated sheets (in which all microspheres were degraded by 3 weeks) and high Gp-incorporated sheets which contained remaining undegraded microspheres. Increased stiffness of the low Gp+TGF-β1 sheets could be attributed to the increased GAG and type II collagen contents. The increased E values of the microsphere-incorporated sheets compared to the control could be partly due to the increased matrix spacing lending to improved water retention within the tissue. All sheets initially incorporated with microspheres had a greater wet mass than control sheets after 3 weeks, suggesting that higher water content could be playing a role in the improved mechanical properties in the microsphere-incorporated sheets. Additionally, the presence of residual high Gp microspheres may have contributed to the enhanced mechanical stiffness of the sheets incorporated with high Gp microspheres.

This membrane-based system of self-assembling hMSCs can be compared to the "macroaggregate" system developed using human nasoseptal or auricular chondrocytes to form cartilage sheets. In the study by Naumann et al., macroaggregates were formed by centrifuging mature chondrocytes onto membranes at a cell density similar to that used in this study, and then cultured in vitro for 3 weeks. The resultant constructs were sturdy enough to be handled at the time of harvest, however, their mechanical properties were not determinable by indentation assay, as the samples failed to reach equilibrium during testing. The authors suggested that this may be due to GAG contents much lower than those of native cartilage, as GAGs are known to contribute to increased tissue stiffness in compression. This result was comparable to our findings for control hMSC sheets without microspheres, which could be peeled from Transwell membranes without tearing but did not demonstrate any change in equilibrium force during stepstrain stress relaxation testing, making it impossible to obtain a measurement for E. However, microsphere-incorporated sheets cultured in exogenous TGF-β1 had GAG levels similar to those of control sheets, yet they demonstrated improved mechanical properties in compression testing. We propose that this may be due to the favorable distribution of GAG-containing matrix leading to increased water content within microsphere-incorporated sheets by comparison to controls, particularly for the low Gp condition in which the microspheres had almost entirely degraded. Though the collagen distributions appeared similar among control and microsphere-incorporated groups, differences in total collagen amount may have also contributed to this result.

Despite the enhancement of mechanical properties by incorporation of microspheres into self-assembling hMSC sheets, these microsphere-incorporated sheets have compressive moduli that are lower than those of normal human articular cartilage. As has been demonstrated in other high density cell systems, it may be possible to increase the stiffness of these constructs with increased time in culture, in perfusion-based bioreactor systems, or with the application of external mechanical stimuli. In addition, since the microsphere-incorporated sheets are easily handled at early times in culture, it may be possible to implant them in vivo, allowing physiological mechanical stimulation to induce cartilage formation and enhance mechanical properties of the neocartilage tissue. The sheets incorporated with TGF-β1 loaded microspheres would be optimal for this application, as they have the potential to induce in vivo differentiation without extended prior in vitro culture. While sheets on the size scale described here could be useful for treating partial-thickness cartilage defects such as those occurring during the early stages of osteoarthritis and also for cartilage reconstruction in the nose and ear, they may need to be thicker to fill a full-thickness chondral defect with a single sheet. To increase the applicability of these sheets for treating full-thickness defects, methods of increasing sheet thickness may include using a higher cell number and/or mass of microspheres, or bioreactor culture. Alternatively, multiple sheets could be stacked to fill a single full-thickness defect. We are currently pursuing several of these strategies to enhance the utility of these microsphere-incorporated sheets for a variety of cartilage repair applications.

Importantly, the system of self-assembling, microsphere-incorporated MSC sheets reported here is versatile, and may accommodate the formation of sheets containing other cells with chondrogenic potential including adipose-derived stem cells or mature chondrocytes. Additionally, the incorporated microspheres could be made from different biopolymer formulations with other physical and biochemical properties and loaded with other bioactive factors such as alternative growth factors, plasmid DNA, and/or siRNA. Microsphere-incorporated sheets could be a new platform system for the engineering of different tissue types in addition to cartilage, based on the cell and polymer types used as well as the bioactive factors selected for delivery.

This Example demonstrates the utility of growth factor-incorporated microspheres as a means of enhancing neocartilage tissue formation in high-density hMSC culture. As evaluated via biochemical assays, histological and immunohistochemical analysis, and biomechanical testing, incorporation of growth-factor releasing microspheres into hMSC sheets enhances the structure and function of the high density cell sheets. Beyond producing sheets with superior mechanical properties and more uniform matrix deposition, there may be further advantages of using growth factor-releasing microspheres for in vivo implantation. By eliminating the need for exogenous growth factor supplementation, incorporation of TGF-β1 loaded microspheres could decrease culture time necessary prior to implantation of neocartilage constructs and may circumvent the problem of loss of the chondrogenic phenotype in vivo by providing prolonged local exposure of hMSCs to growth factor.

Example 2

In this Example, we show the utility of this microsphere-incorporated cell sheet technology to form self-assembled cartilage constructs with hASCs, another promising cell source for tissue engineering applications. First, the influence of growth factor spatial distribution and release kinetics on chondrogenesis within hASC aggregates incorporated with TGF-β1-releasing gelatin microspheres was determined by varying microsphere amount, growth factor concentration, and polymer degradation rate. Self-assembling hASC sheets were then engineered with the goal to develop a system capable of inducing hASC chondrogenesis of more clinically relevant size. We tested the hypotheses that (1) hASCs could self-assemble to form high cell density sheets and undergo chondrogenesis in the presence of exogenous chondrogenic growth factor and (2) growth factor released from gelatin microspheres within these sheets could induce chondrogenesis, forming stable neocartilage constructs without the need for extended in vitro culture. Cartilage formation within hASC sheets without microspheres cultured in TGF-β1-supplemented media and sheets with TGF-β1-containing microsphere formulations determined optimal in the aggregate study was analyzed. hASCs have been shown to successfully selfassemble into sheets for skin and adipose tissue engineering, but this is the first report of hASC sheets for cartilage tissue engineering. Importantly, this system with incorporated growth factor containing microspheres has the potential to enable more rapid in vivo application of hASC cartilage therapies.

Materials and Methods hASC Isolation and Expansion

First passage hASCs from 4 female donors (42.75±7.93 years old with a body mass index of 25.34±4.45 kg/m$^2$) were generously provided in frozen vials from the Pennington Biomedical Research Center (Baton Rouge, La.), where they were isolated as previously described. Briefly, hASCs were isolated from the stromal vascular fraction of human adipose tissue by an enzymatic digestion method. Liposuction waste tissue was digested with 200 units/mg collagenase type I (Worthington Biochemical Products, Lakewood, N.J.) for 40 min at 37° C. The stromal fraction was then isolated by density centrifugation and the stromal cells were plated at 3500 cell/cm2 on tissue culture plastic in Dulbecco's modified Eagle's medium (DMEM)-F12 (BioWhittaker, Suwanee, Ga.) with 10% defined fetal bovine serum (FBS; HyClone, Logan, Utah), 100 U/ml penicillin and 100 μg/ml streptomycin (BioWhittaker, Suwanee, Ga.). Passage 1 (P1) hASCs were cryopreserved in liquid nitrogen in medium containing 80% FBS, 10% DMEM, and 10% dimethylsulfoxide (DMSO; Sigma-Aldrich, St. Louis, Mo.).

Upon thawing, cells were expanded by plating at 8000 cells/cm$^2$ in medium containing DMEM-F12 (HyClone, Logan, Utah), 10% FBS, 100 U/ml penicillin and 100 Jg/ml streptomycin (MP Biomedicals, Solon, Ohio), and 10 ng/ml fibroblast growth factor-2 (FGF-2; R&D Systems, Minneapolis, Minn.). Culture medium was supplemented with FGF-2 as it has been reported to enhance proliferation and chondrogenic potential of hASCs at this concentration. After 80-90% confluency was reached, they were trypsinized and frozen in liquid nitrogen in the same cryopreservation medium described above. Cells were used at P3.

hASC Donor Screening

Chondrogenic differentiation of P3 hASCs from the 4 female donors (46±13 years old) was induced in aggregate culture with exogenously supplemented TGF-β1 (Peprotech, Rocky Hill, N.J.). Cells were expanded in monolayer culture until they were ~90% confluent. Cells from each donor were then trypsinized and suspended at a concentration of 1.25× 10$^6$ cells/ml in a chemically defined medium containing DMEM-HG (Sigma-Aldrich, St. Louis, Mo.) with 1% ITS+ Premix (BD Biosciences, Sparks, Md.), 37.5 μg/ml ascorbate-2-phosphate (Wako USA, Richmond, Va.), 10$^{-7}$ M dexamethasone (MP Biomedicals, Solon, Ohio), 1% non-essential amino acids (HyClone, Logan, Utah), and 1% sodium pyruvate (HyClone, Logan, Utah). Cell suspension aliquots (200 μl) were centrifuged at 500×g for 5 minutes in sterile V-bottom polypropylene plates to form free-floating aggregates. Aggregates were cultured with or without 10 ng/ml of TGF-β1 supplemented in the medium. Medium was changed every other day to give the cells enough time to differentiate and form a well-developed neocartilaginous ECM. At the end of culture, the aggregates were harvested and analyzed to identify the most chondrogenic donor as indicated by GAG production normalized to DNA.

Gelatin Microsphere Synthesis and Characterization

Gelatin microspheres were synthesized as previously described. Briefly, an aqueous solution of 11.1% w/v acidic gelatin (Sigma-Aldrich, St. Louis, Mo.) was added dropwise into 250 ml of preheated (45° C.) olive oil (GiaRussa, Coitsville, Ohio) and stirred on a magnetic stirring plate at 500 RPM for 10 min. The solution temperature was then lowered to 4° C. with constant stirring. 100 ml chilled acetone (4° C.) was added to the stirring solution after 30 minutes and again 1 hour later. The solution was then stirred for 5 min at 1000 RPM. The resulting microspheres were collected by filtration, washed with acetone to remove residual olive oil, and dried overnight at RT.

Microspheres were then crosslinked at room temperature (RT) in an aqueous solution of 1% w/v genipin ("Gp"; Wako USA, Richmond, Va.) for either 2 hours ("low Gp") or 24 hours ("high Gp") to produce microspheres with different crosslinking densities. Crosslinked microspheres were collected by filtration, washed several times with ultrapure deionized water (diH$_2$O), and lyophilized. After lyophilization, crosslinked microspheres were stored at 4° C. until use. Growth factor loading was performed on the day of hASC aggregate or sheet production. Crosslinked microspheres were UV-sterilized for 10 minutes and then soaked in a small volume of a solution containing TGF-β1 in phosphate buffered saline (PBS) at pH 7.4 for 2 hours at 37° C. to allow for the positively charged TGF-β1 to complex with the negatively charged gelatin. A small volume of growth factor solution (less than the equilibrium swelling volume of the microspheres) was used to ensure complete absorption. Empty microspheres without growth factor were hydrated with equivalent volumes of PBS only.

Crosslinked microspheres were characterized as previously described. Microspheres were hydrated in PBS and their diameters were measured from light photomicrographs using Image J (National Institute of Health, Bethesda, Md.) analysis software (N=295, "low Gp"; N=256, "high Gp"). Crosslinking densities were determined by a ninhydrin assay (N=3) as previously described. Briefly, 3 mg of microspheres were hydrated in 100 μl diH$_2$O and incubated for 1 hour at RT. Ninhydrin solution was prepared by mixing 1.05 g citric acid, 0.4 g NaOH, and 0.04 g SnCl 2H$_2$O in 25 ml diH$_2$O with 1 g ninhydrin in 25 ml 2-methoxyethanol on a stir plate for 45 min away from light, and 1 ml was added to the hydrated microspheres. Samples and glycine standards were incubated at 100° C. for 4 min, after which 5 ml of 50% isopropanol was added. The absorbance of 200 μl aliquots was read at 570 nm on a SpectraMax M3 multimode microplate reader (Molecular Devices, Sunnyvale, Calif.). The concentration of free amino groups left within the gelatin microspheres was determined from the glycine standard and normalized by the mass of the sample. The degree of crosslinking was defined by the percentage of amino groups that reacted with genipin during the crosslinking process by comparison to uncrosslinked microspheres with 100% free amino groups.

Microsphere-Incorporated hASC Aggregate Formation

UV-sterilized crosslinked microspheres were rehydrated with PBS or a PBS solution with TGF-β1 (400 ng/mg or 1200 ng/mg microspheres) as described above. Varying amounts of microspheres with or without TGF-β1 were suspended in chemically defined medium with P3 cells from the most chondrogenic donor as defined by highest GAG production normalized to DNA at 3 weeks (1.25×10$^6$ cells/ml). 200 μL aliquots were centrifuged at 500×g for 5 minutes in sterile V-bottom polypropylene plates to form free-floating aggregates. The aggregates were cultured for 2 weeks with medium changed every other day. 10 conditions were studied, in which microsphere loading amount, growth factor loading concentration, and degree of crosslinking were varied (Table 3).

TABLE 3

Conditions for hASC aggregate study. 175 × 77 mm (300 × 300 DPI)

| Group | Microsphere type | Microsphere loading (mg/aggregate) | TGF-β1 loading ng/mg microsphere | Exogenous TGF-β1 (ng/ml) |
|---|---|---|---|---|
| 1 | None | 0 | 0 | 10 |
| 2 | Low Gp | 0.15 (3X) | 0 | 10 |
| 3 | High Gp | 0.15 (3X) | 0 | 10 |
| 4 | Low Gp | 0.15 (3X) | 400 (1X) | 0 |
| 5 | High Gp | 0.15 (3X) | 400 (1X) | 0 |
| 6 | Low Gp | 0.15 (1X) | 400 (1X) | 0 |
| 7 | High Gp | 0.15 (1X) | 400 (1X) | 0 |
| 8 | Low Gp | 0.15 (1X) | 1200 (3X) | 0 |
| 9 | High Gp | 0.15 (1X) | 1200 (3X) | 0 |
| 0 | None | 0 | 0 | 0 | hASC Sheet Formation

P3 cells from the most chondrogenic donor as determined from the screen (donor A) were prepared to form self-assembling hASC sheets with or without incorporated microspheres under conditions similar to those described previously with hMSCs. Sheets without microspheres and/or growth factor were prepared. Similar microsphere and growth factor loading conditions that resulted in the highest GAG and GAG/DNA production in the aggregate study were utilized to form microsphere-incorporated sheets. Briefly, crosslinked microspheres were UV sterilized and soaked in PBS or a PBS solution with TGF-β1 (400 ng/mg microspheres). 1.5 mg microspheres with or without TGF-β1 were suspended with 2×10$^6$ hASCs in 500 μL of the chemically defined medium and allowed to settle onto the membranes of 12 mm Transwell inserts (3 μm pore size; Corning, N.Y. City, N.Y.) for 48 hours in a humidified incubator at 37° C. with 5% CO$_2$. 2 ml of medium was added outside of each Transwell insert. 10 ng/ml TGF-β1 was added only to the media of hASC-only sheets and sheets containing unloaded microspheres. The medium was changed every other day for 3 weeks with TGF-β1 supplemented in the specified conditions (Table 4).

TABLE 4

| Group | Microsphere Type | Microsphere loading (mg/sheet) | TGF-β1 loading (ng/mg microsphere) | Exogenous TGF-β1 (ng/ml) |
|---|---|---|---|---|
| Exogenous (exo.) TGF-β1 | None | 0 | 0 | 10 |
| Low Gp + exo. | Low Gp | 1.5 | 0 | 10 |
| high Gp + exo. | High Gp | 1.5 | 0 | 10 |
| Low Gp + exo. + TGF-β1 | Low Gp | 1.5 | 400 | 0 |
| high Gp + exo. + TGF-β1 | High Gp | 1.5 | 400 | 0 |
| Negative control | none | 0 | 0 | 0 |

Quantitative Analysis

At each time point, aggregates and sheets were harvested for analysis. Two 5 mm-diameter punches from each sheet were frozen until analysis. Four aggregates from each group and one 5 mm-diameter punch obtained from each sheet were used for DNA and glycosaminoglycan (GAG) quantification (N≥3). Samples were digested with papain (Sigma-Aldrich, St. Louis, Mo.) at 65° C. for 2 hours, and DNA and GAG content of digests were quantified with PicoGreen (Invitrogen, Carlsbad, Calif.) and dimethylmethylene blue (DMMB) dye (Sigma-Aldrich, St. Louis, Mo.) assays, respectively.

Histology and Immunohistochemistry

Sheet portions designated for histological examination (N=4 for all, except N=3 for exo. TGF-β1) were fixed in formalin and paraffin-embedded. 5 μm sections were stained as previously described for GAG content via toluidine blue (Thermo Fisher Scientific, Waltham, Mass.) and chondroitin-6-sulfate (C-6-S) with a Fast Green counterstain. Sections were deparaffinized and rehydrated with decreasing concentrations of ethanol then washed with PBS. Their endogenous peroxidase activity was quenched using $H_2O_2$ (30% v/v) and methanol at a ratio of 1:9. Sections for collagen staining were digested with pronase (Sigma-Aldrich, St. Louis, Mo.). Sections for chondroitin-6-sulfate staining were also treated with chondroitinase ABC (Sigma-Aldrich, St. Louis, Mo.) to further expose chondroitin sulfate epitopes. Anti-chondroitin-6-sulfate (Millipore, Billerica, Mass.) was used as the primary antibody, and mouse IgG (Vector Laboratories, Burlingame, Calif.) was used instead of primary antibody as a negative control. The Histostain-Plus Bulk kit (Invitrogen, Carlsbad, Calif.) containing 10% goat non-immune blocking serum, biotinylated secondary antibody, and enhanced horseradish peroxidase (HRP) conjugated streptavidin was used in accordance to manufacturer's instructions. Aminoethyl carbazole (AEC), a HRP substrate/chromogen (Invitrogen, Carlsbad, Calif.) was added to react with the enhanced HRP on the secondary antibody. HRP catalyzes the AEC substrate and converts it to a red deposit. Slides were mounted with glycerol vinyl alcohol (GVA) (Invitrogen, Carlsbad, Calif.) and imaged using an Axio Observer Z1 (Zeiss, Thornwood, N.Y.) inverted fluorescent microscope equipped with a C10600 digital camera (Hamamatsu, Bridgewater, N.J.).

Statistical Analysis

Statistical analysis was performed using InStat 3.06 software (GraphPad Software Inc., La Jolla, Calif.). Microsphere diameters were compared using a nonparametric Mann-Whitney test. All other analyses were performed using one-way ANOVA with Tukey's post hoc tests. Values of $p<0.05$ were considered statistically significant.

Results

DNA and GAG Analysis of hASC Donor Screen

A donor screen was performed to examine the chondrogenic potential of hASCs from 4 female donors, A-D. After 3 weeks of culture, DNA, GAG and GAG/DNA contents were significantly higher for aggregates from donor A cultured with exogenously supplemented TGF-β1 than aggregates cultured in control media without TGF-β1 and those from the other donors (FIG. 8). Interestingly, there was baseline GAG production for aggregates from all donors, even in the absence of TGF-β1. No significant differences in GAG and GAG/DNA contents, however, were found with or without TGF-β1 for donors B, C, and D.

Microsphere Characterization

Hydrated microspheres were roughly spherical with similar average diameters (60.9±50.1 μm, "low Gp"; 54.3±47.9 μm, "high Gp") and non-Gaussian size distributions (FIG. 9). The microspheres that were incubated with genipin for 2 hours were 28.8±6.8% crosslinked and appeared as a light blue color. Those that were incubated with genipin for 24 hours were 64.9±9.9% crosslinked and were a dark blue color.

DNA and GAG Analysis of Microsphere-Incorporated hASC Aggregates

TGF-β1-loaded gelatin microspheres were then incorporated within hASC aggregates from the most chondrogenic donor. Microsphere amount, growth factor concentration, and polymer degradation rate were varied to study the influence of growth factor distribution and release kinetics on hASC chondrogenesis (Table 3). DNA content after 1 week was not significantly different among the 9 groups analyzed (FIG. 10A). Groups 1 through 5 had similar DNA content at 1 and 2 weeks, with the exception of group 3 which had significantly higher DNA than that of group 4 at 2 weeks. However, DNA levels for groups 6 through 9 were significantly lower at week 2 than at week 1. They were also significantly lower than the DNA contents of groups 1 through 5 at week 2. In groups 6 and 7, a lower microsphere loading concentration was used with the same TGF-β1 loading concentration per microsphere as groups 4 and 5, resulting in a lower total amount of TGF-β1 per aggregate. This decrease in microsphere mass led to lower cell viability by week 2 compared to groups 1 through 5. Maintaining the lower microsphere loading concentration while increasing the TGF-β1 loading concentration by a factor of 3 resulted in a similar decrease in DNA content at 2 weeks for groups 8 and 9.

GAG and GAG/DNA contents at week 1 were similar for all groups (FIG. 10B,C). In groups 1 through 5, GAG content was higher at week 2 than week 1, with week 2 GAG content for groups 1 and 3 significantly higher than those at week 1 (FIG. 10B). Average GAG/DNA values at week 2 were also higher than the respective values at week 1 for groups 1 through 5, with statistical significance found for group 2 only (FIG. 10C). There were no significant differences in GAG and GAG/DNA contents among these groups at week 2. Importantly, groups 4 and 5, in which TGF-β1-loaded microspheres were incorporated into the aggregates, were able to induce GAG production at levels similar to control groups in which TGF-β1 was exogenously supplemented (groups 1 through 3). However, GAG and GAG/DNA contents in aggregates of groups 6 through 9 did not increase between weeks 1 and 2 and were significantly lower than the GAG and GAG/DNA levels in groups 1 through 5 after 2 weeks (FIG. 10B, C). Groups 6 through 9 had fewer incorporated microspheres, and even though the TGF-β1 loading concentration in groups 8 and 9 was tripled to yield the same total amount of TGF-β1 per aggregate as in groups 4 and 5, GAG production was still significantly lower than in groups 1 through 5. DNA, GAG, and GAG/DNA contents for groups 6 through 9 were similar at both time points despite the difference in TGF-β1 loading concentration. No significant differences in DNA, GAG, and GAG/DNA contents were found between low Gp and high Gp groups with matching microsphere and growth factor loading concentrations. Results from negative control aggregates in group 10 with neither incorporated microspheres nor exogenous TGF-β1 supplementation are not shown as they either did not survive or undergo chondrogenesis as indicated by their very low DNA and GAG levels.

Quantitative Analysis of Microsphere-Incorporated hASC Sheets

The positive results from the aggregate study led to the development of a larger, more clinically relevant model. Self-assembled hASC sheets cultured in TGF-β1-supplemented medium were engineered. hASC sheets with incorporated TGF-β1-releasing microspheres were also produced. The conditions are summarized in Table 4. After 3 weeks in culture, sheets were harvested and their DNA and GAG contents were measured. DNA content was similar for all groups with the exception of low Gp+TGF-β1, which was significantly lower than the control, low Gp+exo., and high Gp+exo. groups (FIG. 11A). No significant differences were observed in GAG and GAG/DNA contents among the conditions tested (FIG. 11B,C). Negative control sheets lacking microspheres and exogenous growth factor supplementation were also prepared but completely dissociated during the 3 weeks of culture and thus could not be analyzed.

Histology and Immunohistochemistry of Microsphere-Incorporated hASC Sheets

Figure 12:
FIG. 12 illustrates photomicrographs of hASC sheets from donor A stained for toluidine blue. Scale bar=100 μm. 31×5 mm (300×300 DPI).

Cartilage formation within hASC sheets was further confirmed via histological analysis. Regions with the most intense metachromatic toluidine blue staining (purple) of GAG are shown in FIG. 12. Some degree of metachromatic GAG staining was present in all groups. Regions with round chondrocytic morphology could be observed in all groups. In most areas that lacked metachromatic staining, cell phenotype was elongated and fibroblastic. High Gp microspheres (dark purple) in the high Gp+exo. and high Gp+TGF-β1 groups appeared to be in the process of degrading, while the low Gp microspheres initially incorporated into the low Gp+exo. And low Gp+TGF-β1 groups were completed degraded by 3 weeks.

Figure 13:
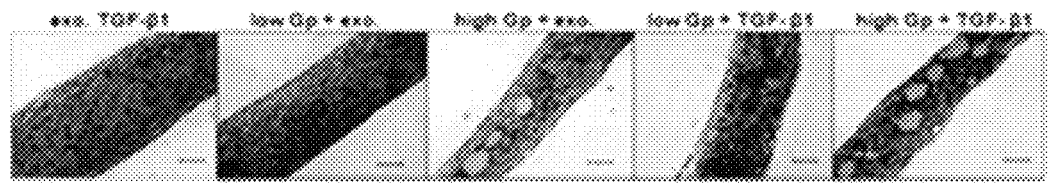
FIG. 13 illustrates photomicrographs of hASC sheets from donor A immunohistochemically stained for chondroitin-6-sulfate (C-6-S). Scale bar=100 #m. 31×5 mm (300×300 DPI).

Immunohistochemistry for chondroitin-6-sulfate, a sulfated GAG that is a major component of cartilage, was performed to further visualize the presence and spatial distribution of GAG as this is a more sensitive method than histochemical staining (FIG. 13). Intense staining for chondroitin-6-sulfate occurred throughout all sheet groups. As with the toluidine blue images, incorporated high Gp microspheres (FIG. 13, "high Gp+exo." and "high Gp+TGF-β1") were still visible while incorporated low Gp microspheres (FIG. 13, "low Gp+exo." and "low Gp+TGF-β1") could not be seen throughout the constructs. No staining occurred for negative control mouse IgG (not shown).

Discussion

This study aimed to explore the influence of growth factor distribution and release kinetics on cartilage formation within high-density hASC aggregates incorporated with TGF-β1-containing microspheres and to engineer larger, more clinically relevant cartilage constructs via the production of self-assembled hASC sheets with or without TGF-β1-loaded microspheres. Incorporation of growth factor releasing biodegradable polymer microspheres within high density hASC constructs may circumvent the need for exogenous growth factor supplementation during in vitro culture by providing spatiotemporal delivery of growth factor to cells within the constructs. Genipin-crosslinked gelatin microspheres were used in this study because they have been shown to locally deliver growth factor at varying rates based on the degree of crosslinking and to promote growth factor-induced cell differentiation and tissue regeneration. Genipin, a natural crosslinking agent, stabilizes gelatin through the covalent binding of primary amine groups [56] with minimal toxic residue production.

After gelatin microspheres with two different crosslinking levels were produced, they were incorporated with or without loaded TGF-β1 within hASC aggregates from the most chondrogenic donor in response to exogenous TGF-β1 as identified in the donor screen. The different degrees of crosslinking were used to regulate cell-mediated degradation and growth factor release profiles. Microsphere and growth factor loading concentrations were varied to determine the influence of growth factor distribution on chondrogenesis within microsphereincorporated hASC aggregates. When TGF-β1 was supplemented in the medium, the presence of microspheres without loaded growth factor did not negatively affect cell viability or GAG production (FIG. 10). DNA, GAG, and GAG/DNA contents in groups 1 (positive control without microspheres), 2 and 3 were similar at each time point and increased GAG production between week 1 and 2 was observed in each group. These results indicate that the incorporated microspheres did not affect cell viability or hASC chondrogenesis.

However, when TGF-β1 was not exogenously supplemented, the amount of incorporated microspheres and concentration of growth factor within the microspheres affected cell survival and GAG production. DNA, GAG, and GAG/DNA contents were similar in all groups after 1 week, but these contents in groups 1 through 5 were significantly higher than those in groups 6 through 9, in which the microsphere and growth factor loading concentrations were varied, after 2 weeks. Increased GAG and GAG/DNA contents from week 1 to week 2 were observed in groups 4 and 5 in which 0.15 mg microspheres loaded with 400 ng TGF-β1 per mg microspheres were incorporated into each aggregate (FIG. 10, groups 4 and 5). DNA, GAG, and GAG/DNA contents in groups 4 and 5 did not differ significantly from those in aggregates cultured in growth factor containing medium (groups 1-3) at either time point, indicating that the incorporated growth factor loaded microspheres had the potential to induce hASC chondrogenesis at levels equivalent to those of groups 1 through 3 in which TGF-β1 was exogenously supplemented.

When the amount of microspheres was reduced by a factor of 3 from 0.15 mg to 0.05 mg but the growth factor concentration per mg microspheres stayed at 400 ng/mg (FIG. 10, groups 6 and 7), DNA level significantly decreased after 1 week and little to no GAG was produced. This may have been a result of the lower total amount of TGF-β1 that was available to the cells. A study by Awad et al. showed that TGF-β1 increases proliferation of hASCs in the presence of ITS+, a component in the culture medium utilized here. Therefore, it makes sense that a lower total amount of TGF-β1 led to decreases in DNA content in aggregates exposed to less total TGF-β1. When the lower microsphere mass was used and TGF-β1 loading concentration was increased by a factor of 3 from 400 ng TGF-β1/mg microspheres to 1200 ng TGF-β1/mg microspheres, DNA, GAG, and GAG/DNA contents were all significantly lower than those in groups 1 through 5 after 2 weeks (FIG. 10, groups 8 and 9) even though the total amount of growth factor per aggregate was the same as in groups 4 and 5. This could be due to diffusion limitations of TGF-β1 from the reduced number of microspheres to distant cells within the aggregates. It is also possible that the high local concentrations of TGF-β1 from the microspheres had a negative impact on chondrogenesis, as it has been reported that high concentrations of TGF-β1 can inhibit the chondrogenic differentiation of hASCs. Results from groups 6 through 9 compared to groups 4 and 5 signify that the appropriate amount of loaded microspheres is necessary to maintain cell viability and achieve hASC chondrogenesis in this system. Increasing growth factor loading concentration to achieve the same total amount of growth factor per aggregate as in groups 4 and 5 did not improve cell survival and GAG production when a lower microsphere mass was used (groups 6 though 9).

No significant differences were found between low Gp and high Gp groups with matching microsphere and growth factor loading concentrations (groups 2 and 3, groups 4 and 5, groups 6 and 7, and groups 8 and 9). This is especially interesting because microspheres with two different levels of crosslinking were used, resulting in different cell-mediated degradation rates. Because the low Gp microspheres have a lower degree of crosslinking, their enzymemediated degradation should be quicker than that of the high Gp microspheres. Since TGF-β1 release is mediated by microsphere degradation, more TGF-β1 may have been released from the low Gp microspheres than from high Gp microspheres by 2 weeks. One would then expect that a higher GAG level would result in the TGF-β1-loaded low Gp group compared to the other groups as has been observed in a related system with hMSCs. However, this was not the case for these hASC aggregates. It is possible this difference in TGF-β1 exposure is not enough to significantly affect hASC chondrogenesis.

To develop constructs of a more clinically relevant size for cartilage regeneration, selfassembling hASC sheets were then engineered. To our knowledge, this is the first report of hASC sheet constructs for cartilage tissue engineering. hASC sheets were created containing cells only and cultured in TGF-β1 supplemented medium, or incorporated with growth factor releasing hydrogel microspheres. Culture time was extended to 3 weeks to give the cells more time to differentiate and secrete a neocartilaginous ECM. For cell-only sheets cultured in TGF β1-containing medium, quantitative biochemical measurements indicated that the constructs remained viable throughout culture as shown by stable DNA content and high GAG content. GAG and GAG/DNA values were comparable to the largest values that have been reported for in vitro hASC chondrogenesis.

Microsphere-incorporated hASC sheets were also produced (Table 4) utilizing similar conditions of TGF-β1-loaded microsphere incorporation to those that promoted the best chondrogenesis in aggregates (from Table 3, groups 4 and 5). DNA, GAG, and GAG/DNA were similar for all conditions including hASC-only sheets with the exception of DNA content for the low Gp+TGF-β1 sheets, which was significantly less than that of the sheets treated with exogenously supplemented growth factor. The equivalent levels of GAG production in low Gp+TGF-β1 sheets and high Gp+TGF-β1 sheets is particularly noteworthy. Because the low Gp microspheres have a lower degree of crosslinking, their enzyme-mediated degradation occurs more rapidly than that of the high Gp microspheres. Since TGF-β1 release is mediated by microsphere degradation, more loaded TGF-β1 may have been released from the low Gp microspheres than the high Gp microspheres by the end of culture. In the comparable system of microsphere-incorporated hMSC sheets, this rapid degradation and complete growth factor release led to increased GAG production in the low Gp+TGF-β1 sheets after 3 weeks. However, this was not the case for the microsphere-incorporated hASC sheets. While the reasoning behind this is unclear, it is possible that this difference in TGF-β1 release is not significant enough to result in different levels of chondrogenesis by the hASCs. It should also be noted that hASCs are a different cell type that responds differently to TGF-β1, and this study further demonstrates the differences between hMSCs and hASCs reponses under similar culture conditions. Overall, these results demonstrate that the presence of microspheres without loaded TGF-β1 had no apparent effect on chondrogenesis, while sheets containing TGF-β1-loaded microspheres achieved levels of chondrogenesis equivalent to those cultured with medium containing TGF-β1.

Negative control hASC sheets with empty microspheres and no exogenous growth factor supplementation were formed but did not survive during the culture period. This indicated that GAG production in the sheets containing TGF-β1-loaded microspheres (low Gp+TGF-β1 and high Gp+TGF-β1) was due to the growth factor released from the incorporated microspheres rather than the presence of the microspheres themselves.

To further confirm cartilage formation within sheets, histological analysis was performed. Despite the relatively high biochemical GAG measurement, metachromatic toluidine blue staining was not uniform throughout the sheets. However, some regions of metachromatic staining and cartilage-like morphological structure were observed in all groups (FIG. 12). Immunohistochemistry against chondroitin-6-sulfate was performed to better visualize GAG production as it is a more specific and more sensitive method than histochemical staining. As expected, intense staining for C-6-S was observed in all groups (FIG. 13). The C-6-S staining serves as additional evidence that the hASCs within this system were able to undergo chondrogenesis and produce a neocartilaginous ECM.

Incorporated low Gp microspheres within the low Gp+exo. and low Gp+TGF-β1 sheet constructs appeared to be completely degraded by 3 weeks. The space left by the degraded low Gp microspheres seemed to have been filled in by cells and ECM. On the other hand, incorporated high Gp microspheres (dark purple (FIG. 12) or dark blue (FIG. 13)) within the high Gp+exo. and high Gp+TGF-β1 groups were still present after 3 weeks. These visual differences confirmed the difference in degradation rates between the low Gp and high Gp microspheres.

The histology of the constructs presented here were not as similar to native cartilage as hMSC-generated cartilage sheets, confirming the findings of several other studies utilizing these cell populations in different systems. For example, one study found that toluidine blue staining of sulfated proteoglycans in exogenously TGF-β1-treated hASC aggregates was weak compared to that of hMSC aggregates. In a study by Diekman et al., the histological Safranin O GAG staining of hASCs cultured for 4 weeks in a cartilage-derived matrix with TGF-β3 and BMP-6 was weak compared to similarly cultured hMSC constructs and the positive control of a human osteochondral plug. An elongated phenotype was described for the hASCs while a more rounded morphology was seen in hMSC-generated cartilage. These findings suggest that more work is needed to identify better soluble factors to drive hASC chondrogenesis. However, such efforts may prove worthwhile, as the high availability of adipose tissue and ability to obtain high numbers of easily expanded hASCs, which can maintain their differentiation capacity, make this an excellent candidate cell source for tissue engineering and regeneration.

Overall, this system of growth factor-releasing biodegradable polymer microspheres incorporated within self-assembled hASC sheets shows great promise for use in cartilage tissue engineering applications. Although significant differences in GAG production between the different types of crosslinked microspheres used in this study were not observed in this system, different growth factors could be used for which the degree of microsphere crosslinking and proteolytic degradation rate can be tuned along with microsphere loading density and growth factor loading concentrations to potentially achieve varying rates and levels of cartilage formation in hASC sheets. As our lab has recently demonstrated the efficacy of TGF-β1 in a related system using hMSCs, TGF-β1 was selected for this proof-of-principle study. It is possible that alternative chondrogenic growth factors or a combination of growth factors, more specifically TGF-β3 and BMP-6 or TGF-β1 and BMP-2, may result in enhanced chondrogenesis compared to any of the factors alone. This approach can be explored in future studies to enhance hASC chondrogenesis within this system.

Conclusion

This proof-of-principle study is the first to report the production of hASC sheets for cartilage tissue engineering. It was demonstrated that TGF-β1-loaded gelatin microspheres can be incorporated within high cell density hASC constructs including aggregates and selfassembled cell sheets. In the cell aggregates, it was found that microsphere and growth factor loading concentrations influenced the degree of chondrogenesis achieved with specific conditions inducing chondrogenesis at levels equivalent to control aggregates cultured with exogenously supplemented TGF-β1, as demonstrated by GAG production at 2 weeks. A larger, more clinically relevant model was then explored via the engineering of self-assembling hASC sheets. hASC sheets cultured in TGF-β1 containing medium for 3 weeks developed into neocartilaginous constructs as confirmed by biochemical and histological analyses. hASC sheets with incorporated growth factor loaded microspheres were also produced. In these sheets, microsphere-mediated TGF-β1 release induced GAG production at levels equivalent to sheets without microspheres cultured in TGF-β1 supplemented medium at 3 weeks. The inclusion of TGF-β1-releasing gelatin microspheres provides sustained, localized growth factor delivery by cell-mediated degradation, overcoming the inefficiencies of exogenously supplementing growth factor in the medium. Future studies could investigate the influence of other chondrogenic growth factors, microsphere loading density and growth factor loading concentration on cartilage formation in self-assembled hASC sheets. This simple system has great clinical potential to enable hASC chondrogenesis and cartilage formation in vivo without prior extended in vitro culture.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, we claim:

1. A tissue construct comprising: a self-assembled, scaffold-free, high-density cell aggregate in the form of a cell sheet, the cell aggregate comprising:
   a plurality of chondrogenic progenitor cells;
   a plurality of biocompatible and degradable nanoparticles and/or microparticles that are incorporated within the cell aggregate, wherein the nanoparticles and/or microparticles comprise a gelatin hydrogel cross-linked with genipin and TGF-beta, wherein said TGF-beta is controllably released by the nanoparticles and/or microparticles; and
   a self-secreted extracellular matrix that promotes adherence of the cells to the nanoparticles and/or microparticles.

2. The tissue construct of claim 1, the microparticles having a diameter of about 20 pm to about 100 pm.

3. The tissue construct of claim 1, the cells being at least about 30%, by volume of the cell aggregate based on the total volume of the cell aggregate.

4. The tissue construct of claim 3, the progenitor cells being isolated from at least one of tendon/ligament tissue, bone morrow, adipose tissue or dental pulp.

5. The tissue construct of claim 1, wherein the construct further comprises one or more additional layers of cells sheets and is in the form of a multi-layer construct.

* * * * *

UNITED STATES PATENT AND TRADEMARK OFFICE
CERTIFICATE OF CORRECTION

PATENT NO. : 10,030,228 B2
APPLICATION NO. : 13/863364
DATED : July 24, 2018
INVENTOR(S) : Eben Alsberg et al.

It is certified that error appears in the above-identified patent and that said Letters Patent is hereby corrected as shown below:

Column 37, Line 17 reads:
"20 pm to about 100 pm."
Should read:
--20 μm to about 100 μm.--

Signed and Sealed this
Eighteenth Day of September, 2018

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Gly Arg Gly Asp Ser Pro
1               5
```